US006833269B2

(12) United States Patent
Carpenter

(10) Patent No.: US 6,833,269 B2
(45) Date of Patent: Dec. 21, 2004

(54) MAKING NEURAL CELLS FOR HUMAN THERAPY OR DRUG SCREENING FROM HUMAN EMBRYONIC STEM CELLS

(75) Inventor: Melissa K. Carpenter, Castro Valley, CA (US)

(73) Assignee: Geron Corporation, Menlo Park, CA (US)

(*) Notice: Subject to any disclaimer, the term of this patent is extended or adjusted under 35 U.S.C. 154(b) by 399 days.

(21) Appl. No.: 09/872,183

(22) Filed: May 31, 2001

(65) Prior Publication Data

US 2002/0039724 A1 Apr. 4, 2002

Related U.S. Application Data

(62) Division of application No. PCT/US01/15861, filed on May 16, 2001, and a division of application No. 09/859,351, filed on May 16, 2001.
(60) Provisional application No. 60/257,608, filed on Dec. 22, 2000, and provisional application No. 60/205,600, filed on May 17, 2000.

(51) Int. Cl.[7] .......................... C12N 5/00; C12N 5/02; C12N 5/08
(52) U.S. Cl. ................. 435/377; 435/325; 435/366; 435/368
(58) Field of Search ................... 435/325, 366, 435/368, 377

(56) References Cited

U.S. PATENT DOCUMENTS

| | | | |
|---|---|---|---|
| 5,639,618 A | 6/1997 | Gay | 435/7.21 |
| 5,672,499 A | 9/1997 | Anderson et al. | 435/240.4 |
| 5,698,829 A | 12/1997 | Ruddick et al. | 435/467 |
| 5,766,948 A | 6/1998 | Gage et al. | 435/368 |
| 5,849,553 A | 12/1998 | Anderson et al. | 435/172.3 |
| 5,851,832 A | 12/1998 | Weiss et al. | 435/368 |
| 5,968,829 A | 10/1999 | Carpenter | 435/467 |
| 5,981,165 A | 11/1999 | Weiss et al. | 435/4 |
| 6,040,180 A | 3/2000 | Johe | 435/377 |
| 6,238,922 B1 | 5/2001 | Uchida | 435/380 |

FOREIGN PATENT DOCUMENTS

| | | |
|---|---|---|
| WO | WO 98/50526 | 11/1998 |
| WO | WO 99/01159 | 1/1999 |
| WO | WO 99/04775 | 2/1999 |
| WO | WO 99/28443 | 6/1999 |
| WO | WO 00/17323 | 3/2000 |
| WO | WO 00/47762 | 8/2000 |
| WO | WO 01/68815 | 9/2001 |
| WO | WO 01/98463 | 12/2001 |

OTHER PUBLICATIONS

Andrews, et al., Retinoic Acid Induces Neuronal Differentiation of a Cloned Haman Embryonal Carcinoma Cell Line in Vitro, Dev. Biol. 103:285 (1984).

Bain, et al., Embryonic Stem Cells Express Neuronal Properties in Vitro, Dev. Biol. 168:342 (1995).

Bain, et al., Retinoic Acid Promotes Neural and Represses Mesodermal Gene Expression in Mouse Embryonic Stem Cells in Culture, Chem. and Biophys. Res. Comm. 223:691 (1996).

Bain, et al., Neural Cells Derived by In Vitro Differentiation of P19 and Embryonic Stem Cells, Perspectives Dev. Neurobio. 5:175 (1998).

Bodnar, et al., Extension of Life–span by Introduction of Telomerase into Normal Human Cells, Science 279:349 (1998).

Brustle, et al., In Vitro–Generated Neural Precursors Participate in Mammalian Brain Development, Proc. Natl. Acad. Sci. USA 94:14809 (1997).

Brustle, et al., Embryonic Stem Cell–Derived Glial Precursors: A Source of Myelinating Transplants, Science 285:754 (1999).

Clarke, et al., Generalized Potential of Adult Neural Stem Cells, Science 288:1660 (2000).

Deacon, et al., Blastula–Stage Stem Cells Can Differentiate into Dopaminergic and Serotonergic Neurons after Transplantation, Exp. Neurol. 149:28 (1998).

Fraichard, et al., In Vitro Differentiationof Embryonic Stem Cells into Glial Cells and Functional Neurons, J. Cell Science 108:3181 (1995).

Kalyani, et al., Cell Lineage In the Developing Neural Tube, Biochem. Cell Biol. 76:1051 (1998).

Lee et al., Efficient Generation of Midbrain and Hindbrain Neurons from Mouse Embryonic Stem Cells, Nat. Biotechnol. 18:675 (2000).

Li, et al., Generation of Purified Neural Precursors from Embryonic Stem Cells by Lineage Selection, Current Biology 8:971.

Ling, et al., Differentiation of Mesencephalic Progenitor Cells into Dopaminergic Neurons by Cytokines, Exp. Neurol. 149:411 (1998).

Liu, et al., Embryonic Stem Cells Differentiate into Oligodendrocytes and Myelinate in Culture and After Spinal Cord Transplantation, PNAS 97:6126 (2000).

(List continued on next page.)

Primary Examiner—Anne-Marie Falk
(74) Attorney, Agent, or Firm—J. Michael Schiff; David J. Earp

(57) ABSTRACT

This invention provides populations of neural progenitor cells, differentiated neurons, glial cells, and astrocytes. The populations are obtained by culturing stem cell populations (such as embryonic stem cells) in a cocktail of growth conditions that initiates differentiation, and establishes the neural progenitor population. The progenitors can be further differentiated in culture into a variety of different neural phenotypes, including dopaminergic neurons. The differentiated cell populations or the neural progenitors can be generated in large quantities for use in drug screening and the treatment of neurological disorders.

43 Claims, 6 Drawing Sheets

OTHER PUBLICATIONS

Figure 1:
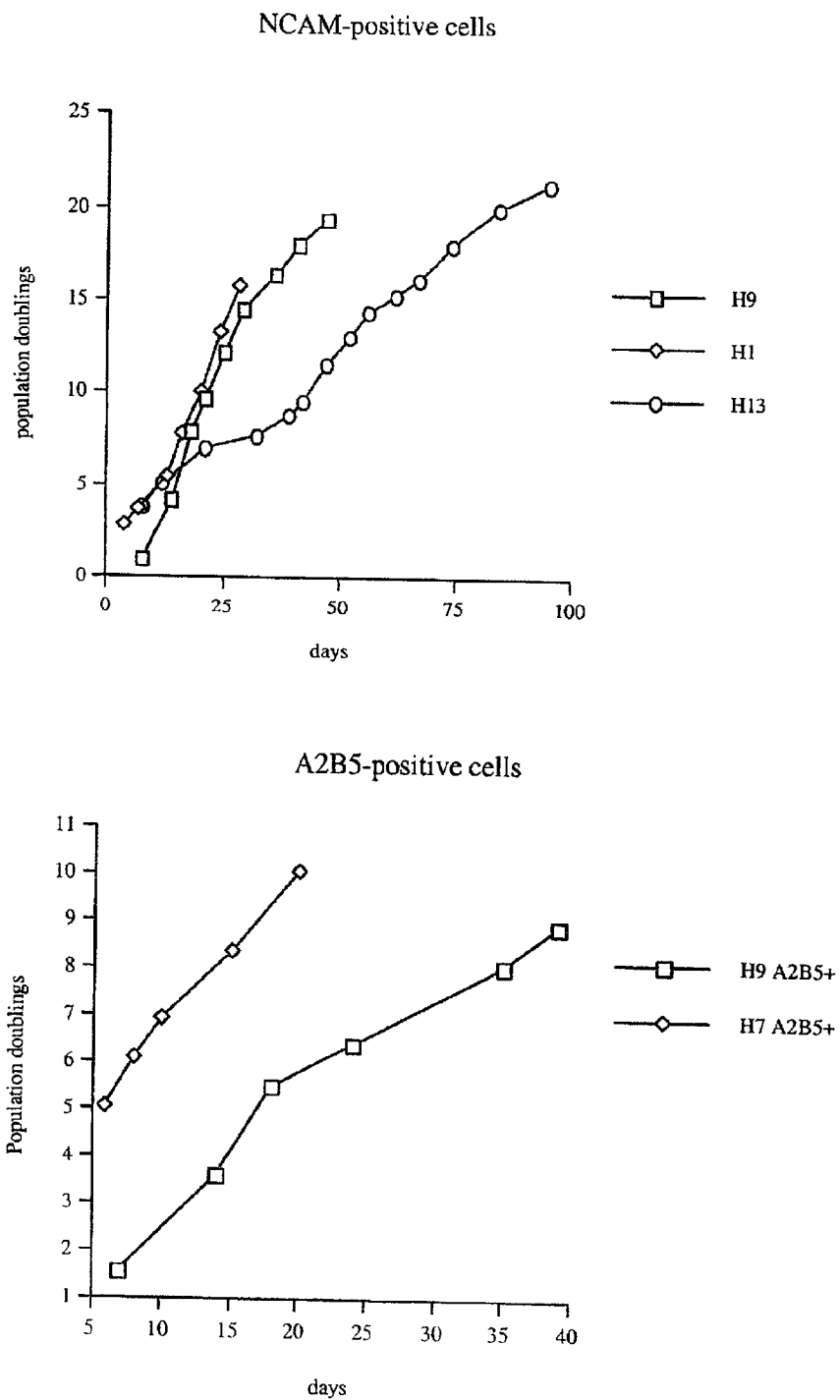

Mayer–Prosche, et al., Isolation of Lineage–Restricted Neuronal Precursors from Mltipotent Neuroepithelial Stem Cells, Neuron 19:773 (1997).

McDonald, et al., Transplanted Embryonic Stem Cells Survive, Differentiate and Promote Recovery in injured Rat Spinal Cord, Nat. Med. 5:1410 (1999).

Mujtaba, et al., Lineage–Restricted Neural Precursors Can Be Isolated from Both the Mouse Neural Tube and Cultured ES Cells, Dev. Biol. 214:113 (1999).

Okabe, et al., Development of Neuronal Precursor Cells and Funcitonal Postmitotic Neurons from Embryonic Stem Cells in Vitro, Mechanisms of Dev. 59:89 (1996).

Reubinoff, et al., Embryonic Stem Cell Lines From Human BlastoCysts: Somatic Differentiation In Vitro, Nature Biotechnol. 18:399 (2000).

Shamblott, et al., Derivation of Pluripotent Stem Cells From Cultured Human Primordial Germ Cells, Proc. Natl. Acad. Sci. USA 95:13726 (1998).

Strubing, et al., Differentiationof Pluripotent Embryonic Stem Cells into the Neuronal Lineage in Vitro Gives Rise to Mature Inhibitory and Excitatory Neurons, Mechanisms of Dev. 53"275 (1995).

Thomson, et al., Neural Differentiation of Rhesus Embryonic Stem Cells, APMIS 106:149 (1998).

Thomson, et al., Embryonic Stem Cell Lines Derived from Human Biastocysts, Science 282:1145 (1998).

Tropepe, et al., Autonomous Neural Cell Fate Specification in Mouse Embryonic Stem Cells—Abstract, Society for Neuroscience 25:527 (1999).

van Inzen, et al., Meuronal Differentiation of Embryonic Stem Cells, Biochimica et Biophsica Acta 1312:21 (1996).

Wagner, et al., Induction of a Midbrain Dopaminergic Phenotype in Nurr1–overexpressing Neural Stem Cells by Type 1 Astrocytes, Nature Biotechnol. 17:653 (1999).

Yao, et al., Neuronal Differentiation of P19 Embryonal Carcinoma cells in Defined Media, J. Neuroscience Res. 41:792 (1995).

Neural Implant Technologies, NeuroInvestment (Dec. 1989).

Lamb, T.M., et al., Neural Induction by the Secreted Polypeptide Noggin, Science 262:713 (1993).

Lim, D.A., et al., Noggin Antagonizes BMP Signaling to Create a Niche for Adult Neurogenesis, Neuron 27:713 (2000).

Sasal, Y., et al., Regulation of Neural Induction by the Chd and Bmp–4 Antagonistic Patturning Signals in Zenopus, Nature 376:333 (1995).

Kalyani, A., et al., Cell Lineage in the Developing Neural Tube, Biochem. Cell Biol. 76:1051 (1998).

Li, M., et al., Generation of Purified Neural precursors from Embryonic Stem Cells by Lineage Selection, Current Biol., Current Science 8:971 (1998).

Mujtaba, T., et al., Lineage–Restricted Neural Precursors Can Be Isolated from Both the Mouse Neural Tube and Cultured ES Cells, Dev. Biol. 214:113 (1999).

Wang S et al, Neural Cells Derived In Culture from Human Embryonic Germ (EG) Cells, Molecular Biology of the Cell, 9: suppl 43TA (Nov) Abstract (XP–001015834).

MAKING NEURAL CELLS FOR HUMAN THERAPY OR DRUG SCREENING FROM HUMAN EMBRYONIC STEM CELLS

REFERENCE TO RELATED APPLICATIONS

This application claims priority to U.S. Provisional Patent Application Ser. Nos. 60/205,600, filed May 17, 2000; and 60/257,608, filed Dec. 22, 2000. This application also claims priority and is a division to an International Application PCT/US01/15861, filed on May 16, 2001, to be published in English 18 months after the first priority date pursuant to Article 21(2) of the PCT. This application is a divisional of pending U.S. utility patent application Ser. No. 09/859,351, filed on May 16, 2001. All four priority applications are hereby incorporated herein by reference in their entirety.

TECHNICAL FIELD

This invention relates generally to the field of cell biology of embryonic cells and neural progenitor cells. More specifically, this invention relates to the directed differentiation of human pluripotent stem cells to form cells of the neuronal and glial lineages, using special culture conditions and selection techniques.

BACKGROUND

Repairing the central nervous system is one of the frontiers that medical science has yet to conquer. Conditions such as Alzheimer's disease, Parkinson's disease, epilepsy, Huntington's disease, and stroke can have devastating consequences for those who are afflicted. Traumatic injury to the head or the spinal chord can instantly propel someone from the bounds of everyday life into the ranks of the disabled.

What makes afflictions of the nervous system so difficult to manage is the irreversibility of the damage often sustained. A central hope for these conditions is to develop cell populations that can reconstitute the neural network, and bring the functions of the nervous system back in line.

For this reason, there is a great deal of evolving interest in neural progenitor cells. Up until the present time, it was generally thought that multipotent neural progenitor cells commit early in the differentiation pathway to either neural restricted cells or glial restricted cells. These in turn are thought to give rise to mature neurons, or to mature astrocytes and oligodendrocytes. Multipotent neural progenitor cells in the neural crest also differentiate to neurons, smooth muscle, and Schwann cells. It is hypothesized that various lineage-restricted precursor cells renew themselves and reside in selected sites of the central nervous system, such as the spinal chord. Cell lineage in the developing neural tube has been reviewed in the research literature by Kalyani et al. (Biochem. Cell Biol. 6:1051, 1998).

Putative multipotent neuroepithelial cells (NEP cells) have been identified in the developing spinal cord. Kalyani et al. (Dev. Biol. 186:202, 1997) reported NEP cells in the rat. Mujtaba et al. (Dev. Biol. 214:113, 1999) reported NEP cells in the mouse. Differentiation of NEP cells is thought to result in formation of restricted precursor cells having characteristic surface markers.

Putative neural restricted precursors (NRP) were characterized by Mayer-Proschel et al. (Neuron 19:773, 1997). These cells express cell-surface PS-NCAM, a polysialylated isoform of the neural cell adhesion molecule. They reportedly have the capacity to generate various types of neurons, but do not form glial cells.

Putative glial restricted precursors (GRPs) were identified by Rao et al. (Dev. Biol. 188: 48, 1997). These cells apparently have the capacity to form glial cells but not neurons.

Ling et al. (Exp. Neurol. 149:411, 1998) isolated progenitor cells from the germinal region of rat fetal mesencephalon. The cells were grown in EGF, and plated on poly-lysine coated plates, whereupon they formed neurons and glia, with occasional tyrosine hydroxylase positive (dopaminergic) cells, enhanced by including IL-1, IL-11, LIF, and GDNF in the culture medium.

Wagner et al. (Nature Biotechnol. 17:653, 1999) reported cells with a ventral mesencephalic dopaminergic phenotype induced from an immortalized multipotent neural stem cell line. The cells were transfected with a Nurr1 expression vector, and then cocultured with VM type 1 astrocytes. Over 80% of the cells obtained were claimed to have a phenotype resembling endogenous dopaminergic neurons.

Mujtaba et al. (supra) reported isolation of NRP and GRP cells from mouse embryonic stem (mES) cells. The NRPs were PS-NCAM immunoreactive, underwent self-renewal in defined medium, and differentiated into multiple neuronal phenotypes. They apparently did not form glial cells. The GRPs were A2B5-immunoreactive, and reportedly differentiated into astrocytes and oligodendrocytes, but not neurons.

A number of recent discoveries have raised expectations that embryonic cells may become a pluripotential source for cells and tissues useful in human therapy. Pluripotent cells are believed to have the capacity to differentiate into essentially all types of cells in the body (R. A. Pedersen, Scientif. Am. 280(4):68, 1999). Early work on embryonic stem cells was done using inbred mouse strains as a model (reviewed in Robertson, Meth. Cell Biol. 75:173, 1997; and Pedersen, Reprod. Fertil. Dev. 6:543, 1994).

Compared with mouse ES cells, monkey and human pluripotent cells have proven to be much more fragile, and do not respond to the same culture conditions. Only recently have discoveries been made that allow primate embryonic cells to be cultured ex vivo.

Thomson et al. (Proc. Natl. Acad. Sci. USA 92:7844, 1995) were the first to successfully culture embryonic stem cells from primates, using rhesus monkeys and marmosets as a model. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998). Both hES and hEG cells have the long-sought characteristics of human pluripotent stem (hPS) cells: they are capable of ongoing proliferation in vitro without differentiating, they retain a normal karyotype, and they retain the capacity to differentiate to produce all adult cell types.

Reubinoff et al. (Nature Biotechnol. 18:399, 2000) reported somatic differentiation of human blastocysts. The cells differentiated spontaneously in culture, with no consistent pattern of structural organization. After culturing for 4–7 weeks to high density, multicellular aggregates formed above the plane of the monolayer. Different cells in the culture expressed a number of different phenotypes, including expression of β-actin, desmin, and NCAM.

Spontaneous differentiation of pluripotent stem cells in culture or in teratomas generates cell populations with a highly heterogeneous mixture of phenotypes, representing a spectrum of different cell lineages. For most therapeutic purposes, it is desirable for differentiated cells to be relatively uniform—both in terms of the phenotypes they express, and the types of progeny they can generate.

Accordingly, there is a pressing need for technology to generate more homogeneous differentiated cell populations from pluripotent cells of human origin.

SUMMARY

This invention provides a system for efficient production of primate cells that have differentiated from pluripotent cells into cells of the neuronal or glial lineage. Populations of cells are described which contain precursors for either lineage, which provide a source for generating additional precursor cells, the mature cells of the central nervous system: neurons, astrocytes, or oligodendrocytes. Certain embodiments of the invention have the ability to generate cells of both lineages. The precursor and mature cells of this invention can be used a number of important applications, including drug testing and therapy to restore nervous system function.

One embodiment of this invention is a cell population that proliferates in an in vitro culture, obtained by differentiating primate pluripotent stem (pPS) cells, wherein at least about 30% of the cells in the population are committed to form neuronal cells, glial cells, or both. A second embodiment is a cell population that proliferates in an in vitro culture, comprising at least about 60% neural progenitor cells, wherein at least 10% of the cells can differentiate into neuronal cells, and at least 10% of the cells can differentiate into glial cells. A third embodiment is a cell population that proliferates in an in vitro culture, comprising at least about 60% neural progenitor cells, wherein at least 10% of the cells express A2B5, and at least 10% of the cells express NCAM.

Certain cell populations of the invention are obtained by differentiating primate pluripotent stem cells, such as human embryonic stem cells. Some are obtained by differentiating stem cells in a medium containing at least two or more ligands that bind growth factor receptors. Some are obtained by differentiating pPS cells in a medium containing growth factors, sorting the differentiated cells for expression of NCAM or A2B5, and then collecting the sorted cells. Certain cell populations are enriched such that at least 70% of the cells express NCAM or A2B5.

Another embodiment of this invention is a cell population comprising mature neurons, astrocytes, oligodendrocytes, or any combination thereof, obtained by further differentiating a precursor cell population of this invention. Some such populations are obtained by culturing neural precursors in a medium containing an activator of cAMP, a neurotrophic factor, or a combination of such factors. As described below, neurons produced by such methods may be capable of exhibiting an action potential, may show gated sodium and potassium channels, and may show calcium flux when administered with neurotransmitters or their equivalents. Included are populations of cells containing a substantial proportion of dopaminergic neurons, detectable for example by staining for tyrosine hydroxylase.

Also embodied in the invention are isolated neural precursor cells, neurons, astrocytes, and oligodendrocytes, obtained by selecting a cell for the desired phenotype from one of the cell populations.

Where derived from an established line of pPS cells, the cell populations and isolated cells of this invention will typically have the same genome as the line from which they are derived. This means that the chromosomal DNA will be over 90% identical between the pPS cells and the neural cells, which can be inferred if the neural cells are obtained from the undifferentiated line through the course of normal mitotic division. Neural cells that have been treated by recombinant methods to introduce a transgene (such as TERT) or knock out an endogenous gene are still considered to have the same genome as the line from which they are derived, since all non-manipulated genetic elements are preserved.

A further embodiment of the invention is a method of screening a compound for neural cell toxicity or modulation, in which a culture is prepared containing the compound and a neural cell or cell population of this invention, and any phenotypic or metabolic change in the cell that results from contact with the compound is determined.

Yet another embodiment of the invention is a method for obtaining a polynucleotide comprising a nucleotide sequence contained in an mRNA more highly expressed in neural progenitor cells or differentiated cells, as described and exemplified further on in this disclosure. The nucleotide sequence can in turn be used to produce recombinant or synthetic polynucleotides, proteins, and antibodies for gene products enriched or suppressed in neural cells. Antibodies can also be obtained by using the cells of this invention as an immunogen or an adsorbent to identify markers enriched or suppressed in neural cells.

A further embodiment of the invention is a method of reconstituting or supplementing central nervous system (CNS) function in an individual, in which the individual is administered with an isolated cell or cell population of this invention. The isolated cells and cell populations can be used in the preparation of a medicament for use in clinical and veterinary treatment. Medicaments comprising the cells of this invention can be formulated for use in such therapeutic applications.

Other embodiments of the invention are methods for obtaining the neural precursor cells and fully differentiated cells of this invention, using the techniques outlined in this disclosure on a suitable stem cell population. Included are methods for producing cell populations containing dopaminergic cells at a frequency of 1%, 3% or 5%—and populations of progenitor cells capable of generating dopaminergic cells at this frequency—from primate embryonic stem cells. This is particularly significant in view of the loss in dopamine neuron function that occurs in Parkinson's disease. The compositions, methods, and techniques described in this disclosure hold considerable promise for use in diagnostic, drug screening, and therapeutic applications.

These and other embodiments of the invention will be apparent from the description that follows.

DRAWINGS

FIG. 1 is a graph representing the growth of cells bearing neural markers that were derived from human embryonic stem cells. The upper panel shows growth of cells maintained in the presence of CNTF, bFGF, and NT3, and then sorted for expression of NCAM. The lower panel shows growth of cells maintained in the presence of EGF, bFGF, PDGF, and IGF-1, and then sorted for expression of A2B5. Four different hES cell lines were used: H1, H7, H9, and H13. The A2B5 selected population has been passaged over 7 times, and can be further differentiated into both neuronal and glial cells.

Figure 2:
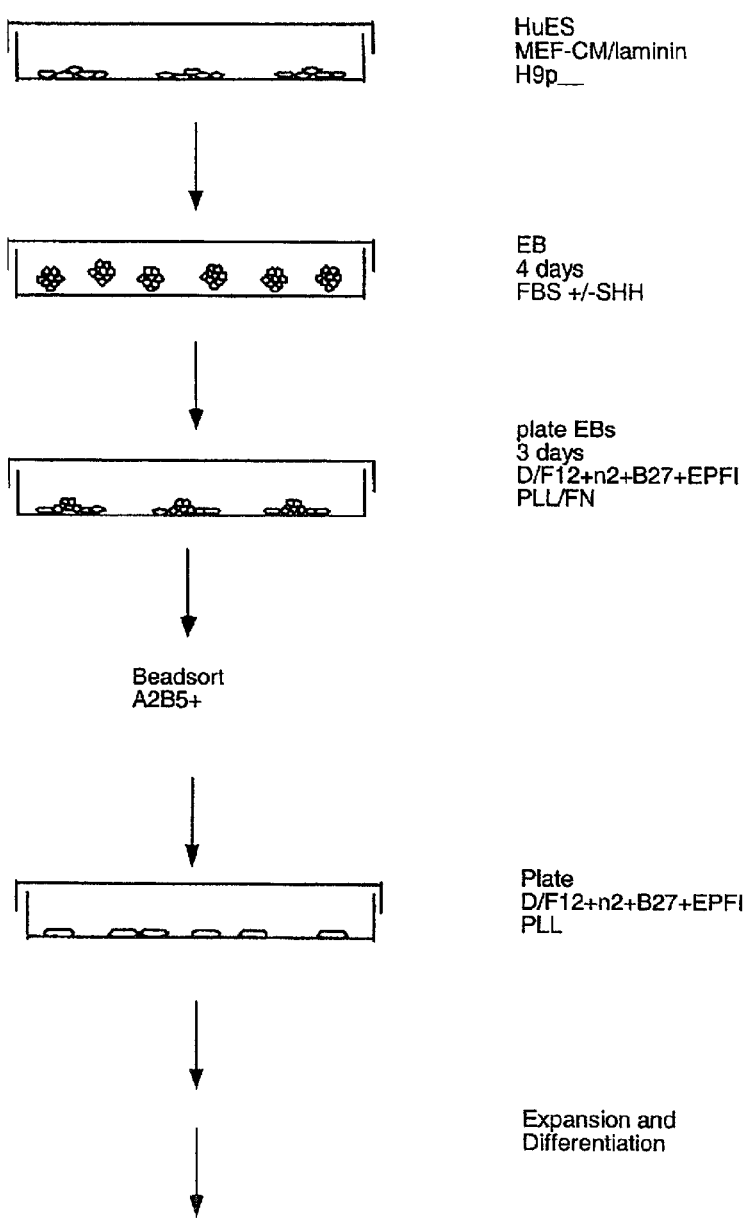

FIG. 2 is a schematic diagram outlining an exemplary procedure for obtaining A2B5-positive cells. Abbreviations used: MEF-CM=medium conditioned by culturing with mouse embryonic fibroblasts; +/−SHH=with or without sonic hedgehog; D/F12=DMEM/F12 medium; N2 and B27, culture supplements (Gibco); EPFI=differentiation agents EGF, PDGF, bFGF, and IGF-1; PLL=poly-L lysine substrate; PLL/FN=substrate of poly-L lysine and fibronectin.

Figure 3:
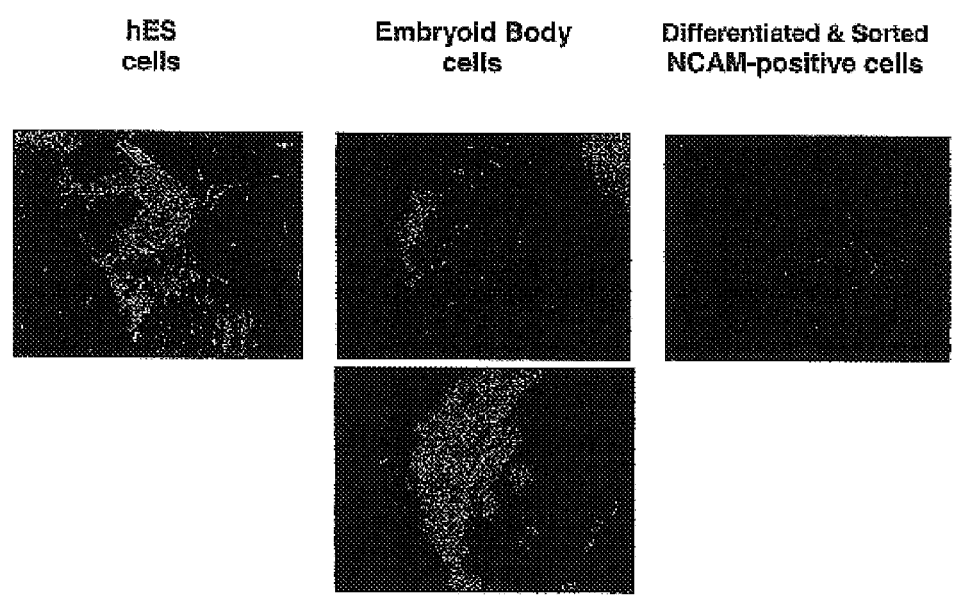

FIG. 3 is a half-tone reproduction of a fluorescence micrograph of the brains from neonatal rats administered with cells that express green fluorescent protein. Left panels: parental hES cell line. Middle panels: embryoid body cells formed from the parental line. Right panels: differentiated cells sorted for expression of NCAM. Undifferentiated hES cells and embryoid body cells remain in the area of administration and show evidence of necrosis. In contrast, the differentiated NCAM+ cells appear as single cells, and have migrated away from the injection site.

Figure 4:

FIG. 4 is a photocopy reproduction of a fluorescence micrograph showing a cell staining for tyrosine hydroxylase (TH), a marker for dopaminergic cells. Embryoid bodies made from human ES cells were maintained in 10 $\mu$m retinoic acid for 4 days, plated into a neural-supportive cocktail, and then passaged into medium containing 10 ng/mL NT-3 and 10 ng/mL BDNF. Certain populations of this invention contain >1% TH-positive cells.

Figure 5:
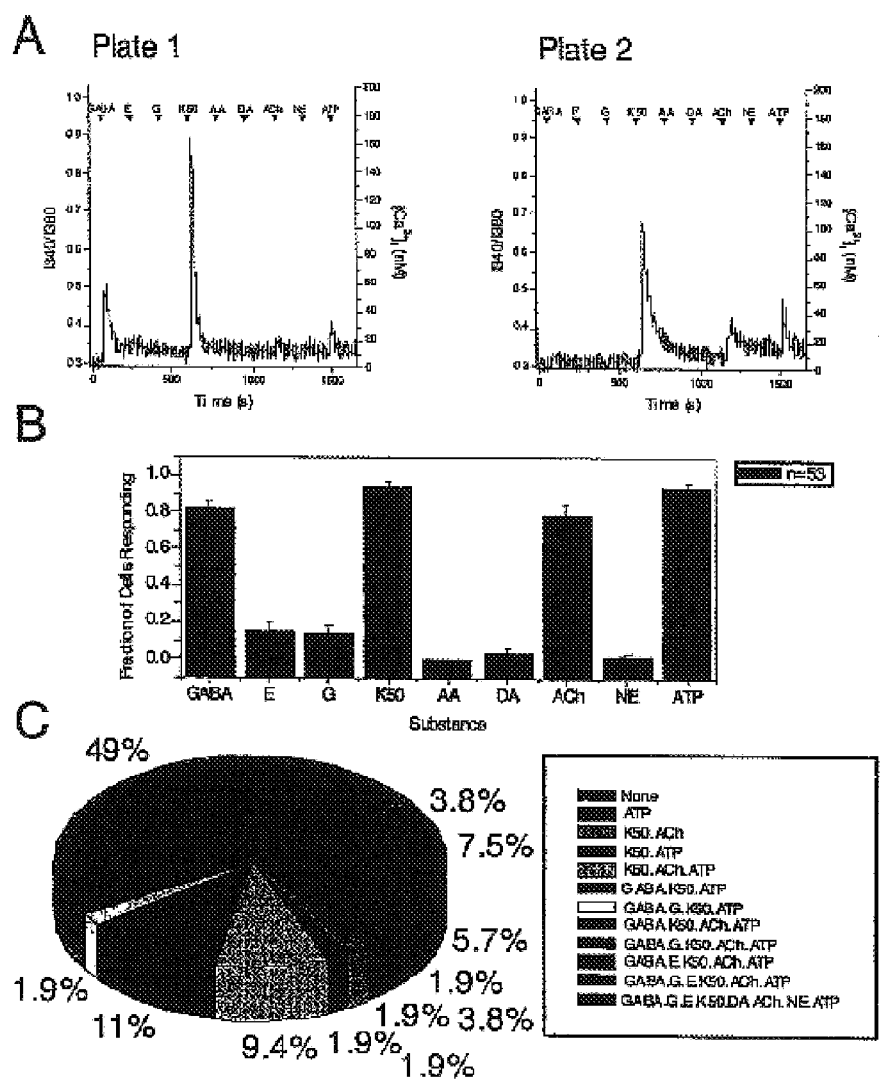

FIG. 5 is a series of graphs showing response of the neural-restricted precursors to various neurotransmitters. Panel A shows the ratio of emission data from single cells on two different coverslips. Both cells responded to GABA, elevated potassium, acetylcholine and ATP. Panel B shows the frequency of cells tested that responded to specific neurotransmitters. Panel C shows the combinations of neurotransmitter responses observed.

Figure 6:
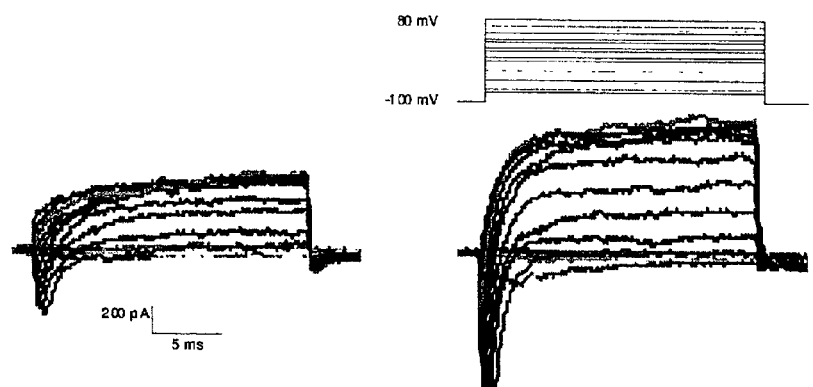
Figure 6:
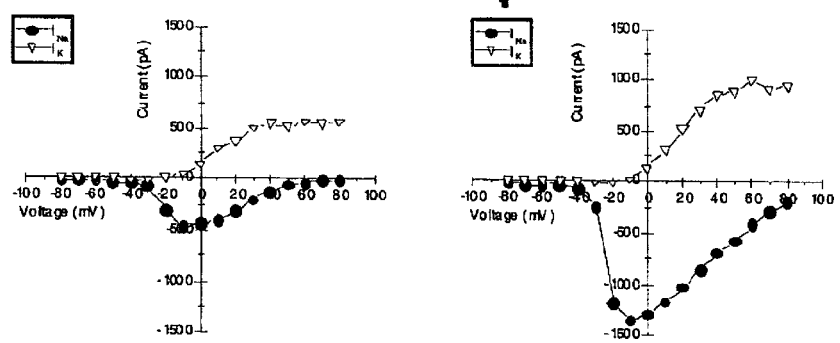
Figure 6:
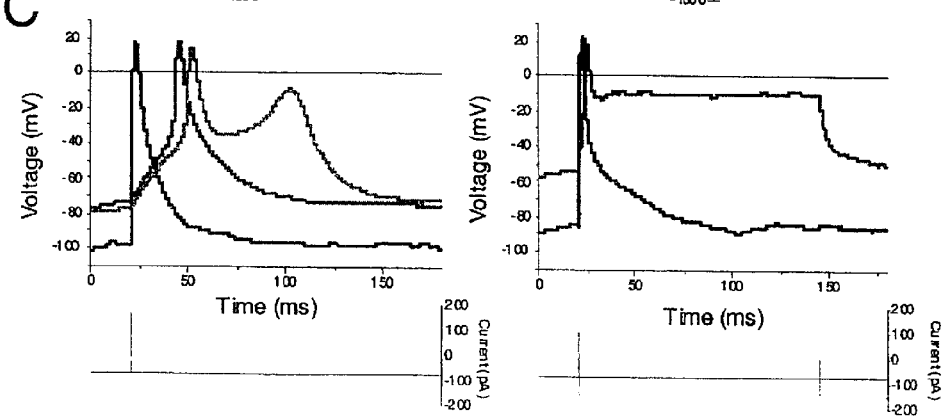

FIG. 6 is a series of graphs showing electrophysiology of neural-restricted precursors. Panel A shows sodium and potassium currents observed in two cells depolarized to test potentials between −80 and 80 mV from a holding potential of −100 mV. Panel B shows the inward (Na+) and outward (K) peak current-voltage relationships observed. Panel C shows action potentials generated by the same cells n response to depolarizing stimuli. These measurements show that neural precursor cells derived from human ES cells are capable of generating action potentials characteristic of neurotransmission.

DETAILED DESCRIPTION

This invention provides a system for preparing and characterizing neural progenitor cells, suitable for use for therapeutic administration and drug screening.

It has been discovered that when pluripotent stem cells are cultured in the presence of selected differentiating agents, a population of cells is derived that has a remarkably high proportion of cells with phenotypic characteristics of neural cells. Optionally, the proportion of neural cells can be enhanced by sorting differentiated cells according to cell-surface markers. Since certain types of pluripotent stem cells (such as embryonic stem cells) can proliferate in culture for a year or more, the invention described in this disclosure provides an almost limitless supply of neural precursors. Certain cell populations of this invention are capable of generating cells of the neuronal or glial lineage, and themselves can be replicated through a large number of passages in culture.

FIG. 1 shows the growth curve of cells that have been cultured with differentiating agents, and then selected according to whether they bear polysialylated NCAM, or the A2B5 epitope. Either of these cell populations can be proliferated through a large number of cell doublings.

Differentiated cells positively selected for A2B5 expression comprise cells that appear to express A2B5 without NCAM, and cells that express A2B5 and NCAM simultaneously. In one of the experiments described below, maturation of these cells produced 13% oligodendrocytes, and 38% neurons. Since these cells proliferate in long-term culture without losing their phenotype, the population can provide a reserve of multipotential cells. Upon administration to a subject with CNS dysfunction, the population would comprise cells that may repopulate both the neuronal and glial cell lineage, as needed.

If desired, the neural precursor cells can be further differentiated ex vivo, either by culturing with a maturation factor, such as a neurotrophic factor, or by withdrawing one or more factors that sustain precursor cell renewal. Neurons, astrocytes, and oligodendrocytes are mature differentiated cells of the neural lineage that can be obtained by culturing the precursor cells in this fashion. The neurons obtained by these methods have extended processes characteristic of this cell type, show staining for neuron-specific markers like neurofilament and MAP-2, and show evidence of synapse formation, as detected by staining for synaptophysin. FIG. 5 shows that these cells respond to a variety of neurotransmitter substances. FIG. 6 shows that these cells are capable of action potentials as measured in a standard patch-clamp system. In all these respects, the cells are apparently capable of full neurological function.

Of particular interest is the ability of this system to generate a supply of dopaminergic neurons (FIG. 4). Cells of this type are particularly desirable for the treatment of Parkinson's disease, for which the best current modality is an allograft of fetal brain tissue. The use of fetal tissue as a clinical therapy is fraught with supply and procedural issues, but no other source described previously can supply the right kind of cells with sufficient abundance. The neural precursor cells of this invention are capable of generating differentiated cells in which several percent of the neurons have a dopaminergic phenotype. This is believed to be a sufficient proportion for cell replacement therapy in Parkinson's disease, and warrants the development of the progenitor populations of this invention for therapeutic use.

Since pluripotent stem cells and some of the lineage-restricted precursors of this invention proliferate extensively in culture, the system described in this disclosure provides an unbounded supply of neuronal and glial cells for use in research, pharmaceutical development, and the therapeutic management of CNS abnormalities. The preparation and utilization of the cells of this invention is illustrated further in the description that follows.

Definitions

For the purposes of this disclosure, the terms "neural progenitor cell" or "neural precursor cell" mean a cell that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage. Typically, they do not produce progeny of other embryonic germ layers when cultured by themselves in vitro, unless dedifferentiated or reprogrammed in some fashion.

A "neuronal progenitor cell" or "neuronal precursor cell" is a cell that can generate progeny that are mature neurons. These cells may or may not also have the capability to generate glial cells.

A "glial progenitor cell" or "glial precursor cell" is a cell that can generate progeny that are mature astrocytes or mature oligodendrocytes. These cells may or may not also have the capability to generate neuronal cells.

A "multipotent neural progenitor cell population" is a cell population that has the capability to generate both progeny that are neuronal cells (such as neuronal precursors or mature neurons), and progeny that are glial cells (such as glial precursors, mature astrocytes, or mature oligodendrocytes), and sometimes other types of cells. The term does not require that individual cells within the population have the capability of forming both types of progeny, although individual cells that are multipotent neural progenitors may be present.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells, such as hematopoetic cells, which are pluripotent for blood cell types; hepatocyte progenitors, which are pluripotent for hepatocytes; and various types of neural progenitors listed above. These in turn can be differentiated further to other types of precursor cells further down the pathway, or to an end-stage differentiated cell, which plays a characteristic role in a certain tissue type, and may or may not retain the capacity to proliferate further. Neurons, astrocytes, and oligodendrocytes are all examples of terminally differentiated cells.

A "differentiation agent", as used in this disclosure, refers to one of a collection of compounds that are used in culture systems of this invention to produce differentiated cells of the neural lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms.

Unless explicitly indicated otherwise, the techniques of this invention can be brought to bear without restriction on any type of progenitor cell capable of differentiating into neuronal or glial cells.

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8–12 week old SCID mice.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. The pPS cells are not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated.

"Feeder cells" or "feeders" are terms used to describe cells of one type that are co-cultured with cells of another type, to provide an environment in which the cells of the second type can grow. For example, certain types of pPS cells can be supported by primary mouse embryonic fibroblasts, immortalized mouse embryonic fibroblasts, or human fibroblast-like cells differentiated from hES cell. pPS cell populations are said to be "essentially free" of feeder cells if the cells have been grown through at least one round after splitting in which fresh feeder cells are not added to support the growth of the pPS.

The term "embryoid bodies" is a term of art synonymous with "aggregate bodies". The terms refer to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

The term "antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs, diabodies, and fusion constructs) as may be prepared by techniques known in the art, and retaining a desired antibody binding specificity.

General Techniques

For further elaboration of general techniques useful in the practice of this invention, the practitioner can refer to standard textbooks and reviews in cell biology, tissue culture, and embryology. Included are *Teratocarcinomas and embryonic stem cells: A practical approach* (E. J. Robertson, ed., IRL Press Ltd. 1987); *Guide to Techniques in Mouse Development* (P. M. Wasserman et al. eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., Reprod. Fertil. Dev. 10:31, 1998).

For elaboration of nervous system abnormalities, and the characterization of various types of nerve cells, markers, and related soluble factors, the reader is referred to *CNS Regeneration: Basic Science and Clinical Advances*, M. H. Tuszynski & J. H. Kordower, eds., Academic Press, 1999.

Methods in molecular genetics and genetic engineering are described in *Molecular Cloning: A Laboratory Manual*, 2nd Ed. (Sambrook et al., 1989); *Oligonucleotide Synthesis* (M. J. Gait, ed., 1984); *Animal Cell Culture* (R. I. Freshney, ed., 1987); the series *Methods in Enzymology* (Academic Press); *Gene Transfer Vectors for Mammalian Cells* (J. M. Miller & M. P. Calos, eds., 1987); *Current Protocols in Molecular Biology and Short Protocols in Molecular Biology, 3rd Edition* (F. M. Ausubel et al., eds., 1987 & 1995); and *Recombinant DNA Methodology II* (R. Wu ed., Academic Press 1995). Reagents, cloning vectors, and kits for genetic manipulation referred to in this disclosure are available from commercial vendors such as BioRad, Stratagene, Invitrogen, and ClonTech.

General techniques used in raising, purifying and modifying antibodies, and the design and execution of immunoassays including immunohistochemistry, the reader is referred to *Handbook of Experimental Immunology* (D. M. Weir & C. C. Blackwell, eds.); *Current Protocols in Immunology* (J. E. Coligan et al., eds., 1991); and R. Masseyeff, W. H. Albert, and N. A. Staines, eds., *Methods of Immunological Analysis* (Weinheim: VCH Verlags GmbH, 1993).

Sources of Stem Cells

This invention can be practiced using stem cells of various types, which may include the following non-limiting examples.

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Except where otherwise required, the invention can be practiced using stem cells of any vertebrate species. Included are stem cells from humans; as well as non-human primates, domestic animals, livestock, and other non-human mammals.

Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells.

Embryonic Stem Cells

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399,2000.

Briefly, human blastocysts are obtained from human in vivo preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1–2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells present in human fetal material taken about 8–11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm$^3$ chunks. The tissue is then pipetted through a 100 μL tip to further disaggregate the cells. It is incubated at 37° C. for ~5 min, then ~3.5 mL EG growth medium is added. EG growth medium is DMEM, 4500 mg/L D-glucose, 2200 mg/L mM NaHCO$_3$;15% ES qualified fetal calf serum (BRL); 2 mM glutamine (BRL); 1 mM sodium pyruvate (BRL); 1000–2000 U/mL human recombinant leukemia inhibitory factor (LIF, Genzyme); 1–2 ng/ml human recombinant bFGF (Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced, incubated 1 h or overnight at 37° C., resuspended in 1–3 mL of EG growth medium, and plated onto a feeder layer.

Ninety-six well tissue culture plates are prepared with a sub-confluent layer of feeder cells (e.g., STO cells, ATCC No. CRL 1503) cultured for 3 days in modified EG growth medium free of LIF, bFGF or forskolin, inactivated with 5000 rad γ-irradiation. ~0.2 mL of primary germ cell (PGC) suspension is added to each of the wells. The first passage is done after 7–10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7–30 days or 1–4 passages.

Propagation of pPS Cells in an Undifferentiated State pPS cells can be propagated continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.).

Traditionally, ES cells are cultured on a layer of feeder cells, typically fibroblasts derived from embryonic or fetal tissue. Embryos are harvested from a CF1 mouse at 13 days of pregnancy, transferred to 2 mL trypsin/EDTA, finely minced, and incubated 5 min at 37° C. 10% FBS is added, debris is allowed to settle, and the cells are propagated in 90% DMEM, 10% FBS, and 2 mM glutamine. To prepare a feeder cell layer, cells are irradiated to inhibit proliferation but permit synthesis of factors that support ES cells (~4000 rads γ-irradiation). Culture plates are coated with 0.5% gelatin overnight, plated with 375,000 irradiated mEFs per well, and used 5 h to 4 days after plating. The medium is replaced with fresh hES medium just before seeding pPS cells.

Scientists at Geron have discovered that pPS cells can alternatively be maintained in an undifferentiated state even without feeder cells. The environment for feeder-free cultures includes a suitable culture substrate, particularly an extracellular matrix such as Matrigel® or laminin. The pPS cells are plated at >15,000 cells cm$^{-2}$ (optimally 90,000 cm$^{-2}$ to 170,000 cm$^{-2}$). Typically, enzymatic digestion is halted before cells become completely dispersed (say, ~5 min with collagenase IV). Clumps of ~10–2000 cells are then plated directly onto the substrate without further dispersal.

Feeder-free cultures are supported by a nutrient medium typically conditioned by culturing irradiated primary mouse embryonic fibroblasts, telomerized mouse fibroblasts, or fibroblast-like cells derived from pPS cells. Medium can be conditioned by plating the feeders at a density of ~5–6×10$^4$ cm$^{-2}$ in a serum free medium such as KO DMEM supplemented with 20% serum replacement and 4 ng/mL bFGF. Medium that has been conditioned for 1–2 days is supplemented with further bFGF, and used to support pPS cell culture for 1–2 days.

Under the microscope, ES cells appear with high nuclear/cytoplasmic ratios, prominent nucleoli, and compact colony formation with poorly discernable cell junctions. Primate ES cells express stage-specific embryonic antigens (SSEA) 3 and 4, and markers detectable using antibodies designated Tra-1-60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pPS cells in vitro results in the loss of SSEA-4, Tra-1-60, and Tra-1-81 expression and increased expression of SSEA-1. SSEA-1 is also found on hEG cells.

Materials and Procedures for Preparing Neural Precursors and Terminally Differentiated Cells Certain neural precursor cells of this invention are obtained by culturing, differentiating, or reprogramming stem cells in a special growth environment that enriches for cells with the desired phenotype (either by outgrowth of the desired cells, or by inhibition or killing of other cell types). These methods are applicable to many types of stem cells, including primate pluripotent stem (pPS) cells described in the previous section.

Typically, the differentiation takes place in a culture environment comprising a suitable substrate, and a nutrient medium to which the differentiation agents are added. Suitable substrates include solid surfaces coated with a positive charge, such as a basic amino acid, exemplified by poly-L-lysine and polyornithine. Substrates can be coated with extracellular matrix components, exemplified by fibronectin. Other permissive extracellular matrixes include Matrigel® (extracellular matrix from Engelbreth-Holm-Swarm tumor cells) and laminin. Also suitable are combination substrates, such as poly-L-lysine combined with fibronectin, laminin, or both.

Suitable differentiation agents include growth factors of various kinds, such as epidermal growth factor (EGF), transforming growth factor α (TGF-α), any type of fibroblast growth factor (exemplified by FGF-4, FGF-8, and basic fibroblast growth factor=bFGF), platelet-derived growth factor (PDGF), insulin-like growth factor (IGF-1 and others), high concentrations of insulin, sonic hedgehog, members of the neurotrophin family (such as nerve growth factor=NGF, neurotrophin 3=NT-3, brain-derived neurotrophic factor=BDNF), bone morphogenic proteins (especially BMP-2 & BMP-4), retinoic acid (RA) and ligands to receptors that complex with gp 130 (such as LIF, CNTF, and IL-6). Also suitable are alternative ligands and antibodies that bind to the respective cell-surface receptors for the aforementioned factors. Typically, a plurality of differentiation agents is used, which may comprise 2, 3, 4, or more of the agents listed above or in the examples below. Exemplary is a cocktail containing EGF, bFGF, PDGF, and IGF-1 (Examples 1 and 2).

The factors are supplied to the cells in a nutrient medium, which is any medium that supports the proliferation or survival of the desired cell type. It is often desirable to use a defined medium that supplies nutrients as free amino acids rather than serum. It is also beneficial to supplement the medium with additives developed for sustained cultures of neural cells. Exemplary are N2 and B27 additives, available commercially from Gibco.

Where the stem cells are pPS cells, the cells (obtained from feeder cell supported or feeder-free cultures) are differentiated by culturing in the presence of a suitable cocktail of differentiation agents.

In one method of affecting differentiation, pPS cells are plated directly onto a suitable substrate, such as an adherent glass or plastic surface, such as coverslips coated with a polyamine. The cells are then cultured in a suitable nutrient medium that is adapted to promote differentiation towards the desired cell lineage. This is referred to as the "direct differentiation" method.

In another method, pPS cells are first let differentiate into a heterogeneous cell population. In an exemplary variation, embryoid bodies are formed from the pPS cells by culturing them in suspension. Optionally, one or more of the differentiation agents listed earlier (such as retinoic acid) can be included in the medium to promote differentiation within the embryoid body. After the embryoid bodies have reached sufficient size (typically 3–4 days), they are plated onto the substrate of the differentiation culture. The embryoid bodies can be plated directly onto the substrate without dispersing the cells. This allows neural cell precursors to migrate out of the embryoid bodies and on to the extracellular matrix. Subsequent passaging of these cultures into an appropriate medium helps select out the neural progenitor cells.

Cells prepared according to these procedures have been found to be capable of further proliferation (Example 1). As many as 30%, 50%, 75% or more of the cells express either polysialylated NCAM or the A2B5 epitope, or both. Typically, at least about 10%, 20%, 30% or 50% of the cells express NCAM, and at least about 10%, 20%, 30% or 50% of the cells express A2B5—which implies that they have the capacity to form cells of the neuronal lineage, and the glial lineage, respectively.

Optionally, the differentiated cells can be sorted based on phenotypic features to enrich for certain populations. Typically, this will involve contacting each cell with an antibody or ligand that binds to a marker characteristic of neural cells, followed by separation of the specifically recognized cells from other cells in the population. One method is immunopanning, in which specific antibody is coupled to a solid surface. The cells are contacted with the surface, and cells not expressing the marker are washed away. The bound cells are then recovered by more vigorous elution. Variations of this are affinity chromatography and antibody-mediated magnetic cell sorting. In a typical sorting procedure, the cells are contacted with a specific primary antibody, and then captured with a secondary anti-immunoglobulin reagent bound to a magnetic bead. The adherent cells are then recovered by collecting the beads in a magnetic field.

Another method is fluorescence-activated cell sorting, in which cells expressing the marker are labeled with a specific antibody, typically by way of a fluorescently labeled secondary anti-immunoglobulin. The cells are then separated individually according to the amount of bound label using a suitable sorting device. Any of these methods permit recovery of a positively selected population of cells that bear the marker of interest, and a negatively selected population of cells that not bear the marker in sufficient density or accessibility to be positively selected. Negative selection can also be effected by incubating the cells successively with a specific antibody, and a preparation of complement that will lyse cells to which the antibody has bound. Sorting of the differentiated cell population can occur at any time, but it has generally been found that sorting is best effected shortly after initiating the differentiation process.

It has been found that cells selected positively for polysialylated NCAM can provide a population that is 60%, 70%, 80%, or even 90% NCAM positive (Example 1). This implies that they are capable of forming some type of neural cell, including neurons.

It has also been found that cells selected positively for A2B5 can provide a population that is 60%, 70%, 80%, or even 90% A2B5 positive (Example 2). This implies that they are capable of forming some type of neural cell, possibly including both neurons and glial cells. The A2B5 positive cells can be sorted again into two separate populations: one that is A2B5 positive and NCAM negative, and one that is both A2B5 positive and NCAM positive.

Differentiated or separated cells prepared according to this procedure can be maintained or proliferated further in any suitable culture medium. Typically, the medium will contain most of the ingredients used initially to differentiate the cells.

If desired, neural precursor cells prepared according to these procedures can be further differentiated to mature neurons, astrocytes, or oligodendrocytes. This can be effected by culturing the cells in a maturation factor, such as forskolin or other compound that elevates intracellular cAMP levels, such as cholera toxin, isobutylmethylxanthine, dibutyladenosine cyclic monophosphate, or other factors such as c-kit ligand, retinoic acid, or neurotrophins. Particularly effective are neurotrophin-3 (NT-3) and brain-derived neurotrophic factor (BDNF). Other candidates are GDNF, BMP-2, and BMP-4. Alternatively or in addition, maturation can be enhanced by withdrawing some or all of the factors that promote neural precursor proliferation, such as EGF or FGF.

For use in therapeutic and other applications, it is often desirable that populations of precursor or mature neurological cells be substantially free of undifferentiated pPS cells. One way of depleting undifferentiated stem cells from the population is to transfect them with a vector in which an effector gene under control of a promoter that causes preferential expression in undifferentiated cells. Suitable promoters include the TERT promoter and the OCT-4 promoter. The effector gene may be directly lytic to the cell (encoding, for example, a toxin or a mediator of apoptosis). Alternatively, the effector gene may render the cell susceptible to toxic effects of an external agent, such as an antibody or a prodrug. Exemplary is a herpes simplex thymidine kinase (tk) gene, which causes cells in which it is expressed to be susceptible to ganciclovir. Suitable pTERT-tk constructs are provided in International Patent Publication WO 98/14593 (Morin et al.).

Characteristics of Neural Precursors and Terminally Differentiated Cells

Cells can be characterized according to a number of phenotypic criteria. The criteria include but are not limited to microscopic observation of morphological features, detection or quantitation of expressed cell markers, enzymatic activity, or neurotransmitters and their receptors, and electrophysiological function.

Certain cells embodied in this invention have morphological features characteristic of neuronal cells or glial cells. The features are readily appreciated by those skilled in evaluating the presence of such cells. For example, characteristic of neurons are small cell bodies, and multiple processes reminiscent of axons and dendrites. Cells of this invention can also be characterized according to whether they express phenotypic markers characteristic of neural cells of various kinds.

Markers of interest include but are not limited to β-tubulin III, microtubule-associated protein 2 (MAP-2), or neurofilament, characteristic of neurons; glial fibrillary acidic protein (GFAP), present in astrocytes; galactocerebroside (GalC) or myelin basic protein (MBP), characteristic of oligodendrocytes; Oct-4, characteristic of undifferentiated hES cells; Nestin, characteristic of neural precursors and other cells; and both A2B5 and polysialylated NCAM, as already described. While A2B5 and NCAM are instructive markers when studying neural lineage cells, it should be appreciated that these markers can sometimes be displayed on other cell types, such as liver or muscle cells. β-Tubulin III was previously thought to be specific for neural cells, but it has been discovered that a subpopulation of hES cells is also β-tubulin III positive. MAP-2 is a more stringent marker for fully differentiated neurons of various types.

Tissue-specific markers listed in this disclosure and known in the art can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for the particular markers listed in this disclosure can be obtained from public database, such as GenBANK. Expression at the mRNA level is said to be "detectable" according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least 2-fold, and preferably more than 10- or 50-fold above that of a control cell, such as an undifferentiated pPS cell, a fibroblast, or other unrelated cell type.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for γ-amino butyric acid (GABA), glutamate, dopamine, 3,4-dihydroxyphenylalanine (DOPA), noradrenaline, acetylcholine, and serotonin.

Differentiation of particular neural precursor cell populations of this invention (for example, using NT-3 and BDNF) can generate cell populations that are at least 20%, 30%, or 40% MAP-2 positive. A substantial proportion, say 5%, 10%, 25%, or more of the NCAM or MAP-2 positive cells will be capable of synthesizing a neurotransmitter, such as acetylcholine, glycine, glutamate, norepinephrine, serotonin, or GABA.

Certain populations of the invention contain NCAM or MAP-2 positive cells that are 0.1%, and possibly 1%, 3%, or 5% or more (on a cell count basis) that are positive for tyrosine hydroxylase (TH), measured by immunocytochemistry or mRNA expression. This generally considered in the art to be a marker for dopamine synthesizing cells.

To elucidate further mature neurons present in a differentiated population, the cells can be tested according to functional criteria. For example, calcium flux can be measured by any standard technique, in response to a neurotransmitter, or other environmental condition known to affect neurons in vivo. First, neuron-like cells in the population are identified by morphological criteria, or by a marker such as NCAM. The neurotransmitter or condition is then applied to the cell, and the response is monitored (Example 6). The cells can also be subjected to standard patch-clamp techniques, to determine whether there is evidence for an action potential, and what the lag time is between applied potential and response. Differentiation of neural precursor populations of this invention can generate cultures that contain subpopulations that have morphological characteristics of neurons, are NCAM or MAP-2 positive, and show responses with the following frequency: a response to GABA, acetylcholine, ATP, and high sodium concentration in at least about 40%, 60% or 80% of the cells; a response to glutamate, glycine, ascorbic acid, dopamine, or norepinephrine in at least about 5%, 10% or 20% of the cells. A substantial proportion of the NCAM or MAP-2 positive cells (at least about 25%, 50%, or 75%) can also show evidence of an action potential in a patch-clamp system.

Other desirable features consistent with functioning neurons, oligodendrocytes, astrocytes, and their precursors can also be performed according to standard methods to confirm the quality of a cell population according to this invention, and optimize conditions for proliferation and differentiation of the cells.

Telomerization of Neural Precursors

It is desirable that neural precursors have the ability to replicate in certain drug screening and therapeutic applications, and to provide a reservoir for the generation of differentiated neuronal and glial cells. The cells of this invention can optionally be telomerized to increase their replication potential, either before or after they progress to restricted developmental lineage cells or terminally differentiated cells. pPS cells that are telomerized may be taken down the differentiation pathway described earlier; or differentiated cells can be telomerized directly.

Cells are telomerized by genetically altering them by transfection or transduction with a suitable vector, homologous recombination, or other appropriate technique, so that they express the telomerase catalytic component (TERT), typically under a heterologous promoter that increases telomerase expression beyond what occurs under the endogenous promoter. Particularly suitable is the catalytic component of human telomerase (hTERT), provided in International Patent Application WO 98/14592. For certain applications, species homologs like mouse TERT (WO 99/27113) can also be used. Transfection and expression of telomerase in human cells is described in Bodnar et al., Science 279:349, 1998 and Jiang et al., Nat. Genet. 21:111, 1999. In another example, hTERT clones (WO 98/14592) are used as a source of hTERT encoding sequence, and spliced into an EcoRI site of a PBBS212 vector under control of the MPSV promoter, or into the EcoRI site of commercially available pBABE retrovirus vector, under control of the LTR promoter.

Differentiated or undifferentiated pPS cells are genetically altered using vector containing supernatants over a 8–16 h period, and then exchanged into growth medium for 1–2 days. Genetically altered cells are selected using 0.5–2.5 µg/mL puromycin, and recultured. They can then be assessed for hTERT expression by RT-PCR, telomerase activity (TRAP assay), immunocytochemical staining for hTERT, or replicative capacity. The following assay kits are available commercially for research purposes: TRAPeze® XL Telomerase Detection Kit (Cat. s7707; Intergen Co., Purchase N.Y.); and TeloTAGGG Telomerase PCR ELISAplus (Cat. 2,013,89; Roche Diagnostics, Indianapolis Ind.). TERT expression can also be evaluated at the mRNA by RT-PCR. Available commercially for research purposes is the LightCycler TeloTAGGG hTERT quantification kit (Cat. 3,012,344; Roche Diagnostics). Continuously replicating colonies will be enriched by further culturing under conditions that support proliferation, and cells with desirable phenotypes can optionally be cloned by limiting dilution.

In certain embodiments of this invention, pPS cells are differentiated into multipotent or committed neural precursors, and then genetically altered to express TERT. In other embodiments of this invention, pPS cells are genetically altered to express TERT, and then differentiated into neural precursors or terminally differentiated cells. Successful modification to increase TERT expression can be determined by TRAP assay, or by determining whether the replicative capacity of the cells has improved.

Other methods of immortalizing cells are also contemplated, such as transforming the cells with DNA encoding myc, the SV40 large T antigen, or MOT-2 (U.S. Pat. No. 5,869,243, International Patent Applications WO 97/32972 and WO 01/23555). Transfection with oncogenes or oncovirus products is less suitable when the cells are to be used for therapeutic purposes. Telomerized cells are of particular interest in applications of this invention where it is advantageous to have cells that can proliferate and maintain their karyotype—for example, in pharmaceutical screening, and in therapeutic protocols where differentiated cells are administered to an individual in order to augment CNS function.

Use of Neural Precursors and Terminally Differentiated Cells

This invention provides a method to produce large numbers of neural precursor cells and mature neuronal and glial cells. These cell populations can be used for a number of important research, development, and commercial purposes.

The cells of this invention can be used to prepare a cDNA library relatively uncontaminated with cDNA preferentially expressed in cells from other lineages. For example, multipotent neural progenitor cells are collected by centrifugation at 1000 rpm for 5 min, and then mRNA is prepared from the pellet by standard techniques (Sambrook et al., supra). After reverse transcribing into cDNA, the preparation can be subtracted with cDNA from any or all of the following cell types: cells committed to the neuronal or glial cell lineage, mature neurons, astrocytes, oligodendrocytes, or other cells of undesired specificity. This produces a select cDNA library, reflecting transcripts that are preferentially expressed in neuronal precursors compared with terminally differentiated cells. In a similar fashion, cDNA libraries can be made that represent transcripts preferentially expressed in neuronal or glial precursors, or mature neurons, astrocytes, and oligodendrocytes.

The differentiated cells of this invention can also be used to prepare antibodies that are specific for markers of multipotent neural progenitors, cells committed to the neuronal or glial cell lineage, and mature neurons, astrocytes, and oligodendrocytes. This invention provides an improved way of raising such antibodies because cell populations are enriched for particular cell types compared with pPS cell cultures, and neuronal or glial cell cultures extracted directly from CNS tissue.

Polyclonal antibodies can be prepared by injecting a vertebrate animal with cells of this invention in an immunogenic form. Production of monoclonal antibodies is described in such standard references as Harrow & Lane (1988), U.S. Pat. Nos. 4,491,632, 4,472,500 and 4,444,887, and *Methods in Enzymology* 73B:3 (1981). Other methods of obtaining specific antibody molecules (optimally in the form of single-chain variable regions) involve contacting a library of immunocompetent cells or viral particles with the target antigen, and growing out positively selected clones. See Marks et al., *New Eng. J. Med.* 335:730, 1996, International Patent Applications WO 94/13804, WO 92/01047, WO 90/02809, and McGuiness et al., *Nature Biotechnol.* 14:1449, 1996. By positively selecting using pPS of this invention, and negatively selecting using cells bearing more broadly distributed antigens (such as differentiated embryonic cells) or adult-derived stem cells, the desired specificity can be obtained. The antibodies in turn can be used to identify or rescue neural cells of a desired phenotype from a mixed cell population, for purposes such as costaining during immunodiagnosis using tissue samples, and isolating precursor cells from terminally differentiated neurons, glial cells, and cells of other lineages.

Gene Expression Analysis

The cells of this invention are also of interest in identifying expression patterns of transcripts and newly synthesized proteins that are characteristic for neural precursor cells, and may assist in directing the differentiation pathway or facilitating interaction between cells. Expression patterns of the differentiated cells are obtained and compared with control cell lines, such as undifferentiated pPS cells, other types of committed precursor cells (such as pPS cells differentiated towards other lineages, cells committed to the neuronal or glial cell lineage), other types of putative neural stem cells such as those obtained from neural crest, neurospheres, or spinal chord, or terminally differentiated cells, such as mature neurons, astrocytes, oligodendrocytes, smooth muscle cells, and Schwann cells.

Suitable methods for comparing expression at the protein level include the immunoassay or immunohistochemistry techniques described above. Suitable methods for comparing expression at the level of transcription include methods of differential display of mRNA (Liang, Peng, et al., Cancer Res. 52:6966, 1992), whole-scale sequencing of cDNA libraries, and matrix array expression systems.

The use of microarray in analyzing gene expression is reviewed generally by Fritz et al Science 288:316, 2000; "Microarray Biochip Technology", L Shi, www.GeneChips.com. Systems and reagents for performing microarray analysis are available commercially from companies such as Affymetrix, Inc., Santa Clara Calif.; Gene Logic Inc., Columbia Md.; HySeq Inc., Sunnyvale Calif.; Molecular Dynamics Inc., Sunnyvale Calif.; Nanogen, San Diego Calif.; and Synteni Inc., Fremont Calif. (acquired by Incyte Genomics, Palo Alto Calif.).

Solid-phase arrays are manufactured by attaching the probe at specific sites either by synthesizing the probe at the desired position, or by presynthesizing the probe fragment and then attaching it to the solid support (U.S. Pat. Nos. 5,474,895 and 5,514,785). The probing assay is typically conducted by contacting the array by a fluid potentially containing the nucleotide sequences of interest under suitable conditions for hybridization conditions, and then determining any hybrid formed.

An exemplary method is conducted using a Genetic Microsystems array generator, and an Axon GenePix™ Scanner. Microarrays are prepared by first amplifying cDNA fragments encoding marker sequences to be analyzed, and spotted directly onto glass slides To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. he slide is then scanned at wavelengths appropriate for each of the labels, the resulting fluorescence is quantified, and the results are formatted to give an indication of the relative abundance of mRNA for each marker on the array.

Identifying expression products for use in characterizing and affecting differentiated cells of this invention involves analyzing the expression level of RNA, protein, or other gene product in a first cell type, such as a pluripotent neuronal precursor cell of this invention, or a cell capable of differentiating along the neuronal or glial pathway; then analyzing the expression level of the same product in a control cell type; comparing the relative expression level between the two cell types, (typically normalized by total protein or RNA in the sample, or in comparison with another gene product expected to be expressed at a similar level in both cell types, such as a house-keeping gene); and then identifying products of interest based on the comparative expression level.

Drug Screening

Neural precursor cells of this invention can be used to screen for factors (such as solvents, small molecule drugs, peptides, polynucleotides) or environmental conditions (such as culture conditions or manipulation) that affect the characteristics of neural precursor cells and their various progeny.

In some applications, pPS cells (undifferentiated or differentiated) are used to screen factors that promote maturation into neural cells, or promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on neural tissue or nerve transmission. Screening may be done either because the compound is designed to have a pharmacological effect on neural cells, or because a compound designed to have effects elsewhere may have unintended side effects on the nervous system. The screening can be conducted using any of the neural precursor cells or terminally differentiated cells of the invention, such as dopaminergic, serotonergic, cholinergic, sensory, and motor neurons, oligodendrocytes, and astrocytes.

The reader is referred generally to the standard textbook "In vitro Methods in Pharmaceutical Research", Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375–410 in "In vitro Methods in Pharmaceutical Research," Academic Press, 1997) for further elaboration.

Effect of cell function can be assessed using any standard assay to observe phenotype or activity of neural cells, such as receptor binding, neurotransmitter synthesis, release or uptake, electrophysiology, and the growing of neuronal processes or myelin sheaths—either in cell culture or in an appropriate model.

Therapeutic Use

This invention also provides for the use of neural precursor cells to restore a degree of central nervous system (CNS) function to a subject needing such therapy, perhaps due to an inborn error in function, the effect of a disease condition, or the result of an injury.

To determine the suitability of neural precursor cells for therapeutic administration, the cells can first be tested in a suitable animal model. At one level, cells are assessed for their ability to survive and maintain their phenotype in vivo. Neural precursor cells are administered to immunodeficient animals (such as nude mice, or animals rendered immunodeficient chemically or by irradiation) at an observable site, such as in the cerebral cavity or in the spinal chord. Tissues are harvested after a period of a few days to several weeks or more, and assessed as to whether pPS derived cells are still present.

This can be performed by administering cells that express a detectable label (such as green fluorescent protein, or β-galactosidase); that have been prelabeled (for example, with BrdU or [$^3$H]thymidine), or by subsequent detection of a constitutive cell marker (for example, using human-specific antibody). Where neural precursor cells are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Various animal models for testing restoration of nervous system function are described in "CNS Regeneration: Basic Science and Clinical Advances", M. H. Tuszynski & J. H. Kordower, eds., Academic Press, 1999.

Differentiated cells of this invention can also be used for tissue reconstitution or regeneration in a human patient in need thereof. The cells are administered in a manner that permits them to graft or migrate to the intended tissue site and reconstitute or regenerate the functionally deficient area.

Certain neural progenitor cells embodied in this invention are designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

By way of illustration, neural stem cells are transplanted directly into parenchymal or intrathecal sites of the central nervous system, according to the disease being treated. Grafts are done using single cell suspension or small aggregates at a density of 25,000–500,000 cells per $\mu$L (U.S. Pat. No. 5,968,829). The efficacy of transplants of motor neurons or their precursors can be assessed in a rat model for acutely injured spinal cord as described by McDonald et al. (Nat. Med. 5:1410, 1999). A successful transplant will show transplant-derived cells present in the lesion 2–5 weeks later, differentiated into astrocytes, oligodendrocytes, and/or neurons, and migrating along the cord from the lesioned end, and an improvement in gate, coordination, and weight-bearing.

The neural progenitor cells and terminally differentiated cells according to this invention can be supplied in the form of a pharmaceutical composition, comprising an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000.

The composition may optionally be packaged in a suitable container with written instructions for a desired purpose, such as the reconstitution of CNS function to improve some neurological abnormality.

The Following Examples are Provided as Further Non-limiting Illustrations of Particular Embodiments of the Invention.

EXAMPLES

Experimental Procedures

This section provides details of some of the techniques and reagents used in the Examples below.

hES cells are maintained either on primary mouse embryonic fibroblasts, or in a feeder-free system. The hES cells are seeded as small clusters either on irradiated mouse embryonic fibroblasts, or on plates coated with Matrigel® (1:10 to 1:30 in culture medium). hES cell cultures on feeder cells are maintained in a medium composed of 80% KO DMEM (Gibco) and 20% Serum Replacement (Gibco), supplemented with 1% non-essential amino acids, 1 mM glutamine, 0.1 mM β-mercaptoethanol and 4 ng/mL human bFGF (Gibco). Cultures free of feeder cells are maintained in the same medium that has previously been conditioned by culturing with embryonic fibroblasts, and resupplemented with 4 ng/mL bFGF (replaced daily).

Cells are expanded by serial passaging. The monolayer culture of ES colonies is treated with 1 mg/mL collagenase for 5–20 minutes at 37° C. The cultures are then gently scraped to remove the cells. The clusters are gently dissociated, and replated as small clusters onto fresh feeder cells.

Embryoid bodies are produced as follows. Confluent monolayer cultures of hES cells are harvested by incubating in 1 mg/mL collagenase for 5–20 min, following which the cells are scraped from the plate. The cells are then dissociated into clusters and plated in non-adherent cell culture plates (Costar) in a medium composed of 80% KO ("knockout") DMEM (Gibco) and 20% non-heat-inactivated FBS (Hyclone), supplemented with 1% non-essential amino acids, 1 mM glutamine, 0.1 mM β-mercaptoethanol. The cells are seeded at a 1:1 or 1:2 ratio in 2 mL medium per well (6 well plate). The EBs are fed every other day by the addition of 2 mL of medium per well. When the volume of medium exceeds 4 mL/well, the EBs are collected and resuspended in fresh medium. After 4–8 days in suspension, the EBs are plated onto a substrate and allowed to differentiate further, in the presence of selected differentiation factors.

Differentiating into neural precursors is typically performed on wells coated with fibronectin (Sigma) at a final concentration of 20 μg/mL in PBS. Using 1 mL/well (9.6 cm$^2$), plates are incubated at 4° C. overnight or at room temperature for 4 h. The fibronectin is then removed, and the plates are washed with PBS or KO DMEM once before use.

Immunocytochemistry for NCAM and A2B5 expression is conducted as follows: Live cells are incubated in primary antibody diluted in culture medium with 1% goat serum for 15 minutes at 37° C., washed once with medium, and then incubated with labeled secondary antibody for 15 min. After washing, the cells are then fixed for 15–20 min in 2% paraformaldehyde. For other markers, cultures are fixed for 10–20 min with 4% paraformaldehyde in PBS, washed 3 times with PBS, permeabilized for 2 min in 100% ethanol, and washed with 0.1 M PBS. Cultures are then incubated in a blocking solution of 0.1 M PBS with 5% NGS (normal goat serum) for at least 1 hour at room temperature. Cultures are then incubated in primary antibody diluted in 0.1 M PBS containing 1% NGS for at least 2 h at room temperature. They are then washed in PBS before a 30 min incubation with secondary antibody in the same buffer. Antibodies used include those shown in Table 1.

TABLE 1

Antibody for Neural Cell Phenotypic Markers

| Antibody | Isotype | Working Dilution | Epitope Specificity | Source |
| --- | --- | --- | --- | --- |
| 5A5 | mouse IgM | 1:1 | Polysialylated NCAM | Developmental studies hybridoma bank |
| A2B5 | mouse IgM | 1:1 | ganglioside | ATCC - CRL1520 clone 105 |
| β-tubulin | IgG | 1:1000 | | Sigma T-8660 |
| GFAP | rabbit polyclonal IgG | 1:500 | | DAKO 2-334 |
| GalC | mouse IgG3 | 1:25 | | Boehringer 1351-621 |

Bead immunosorting is conducted using the following reagents and equipment: magnetic cell separator; Midi MACs™ column; buffer of PBS CMF containing 0.5% BSA and 2 mM EDTA; primary antibody against NCAM or A2B5; rat anti-mouse IgG (or IgM) microbeads; pre-separation filter; rat anti-mouse kappa PE; and a FACScan device. Cells are harvested using trypsin/EDTA (Gibco) and dissociated. After removing the trypsin, the cells are resuspended in MACS™ buffer. Cells are then labeled with primary antibody for 6–8 min at room temp., and washed 2 times in MACs™ buffer by spinning cells at 300×g for 10 min and aspirating the buffer. The cells are then resuspended in 80 μl (minimum vol.) per 10$^7$ cells. 20 μl (minimum vol.) MACs ram™ IgG microbeads per 10$^7$ cells are added for 15 min at 6–12° C. The sample is then washed 2 times in MACS™ buffer before magnetic separation. With the column in the magnetic cell separator, the cell suspension is applied to the column (LS+Midi) in ~3–5 mL buffer. Negative cells are passed through by washing 3 times with 3 mL of MACs™ buffer. The column is then removed from the magnetic field, and positive cells are eluted with 5 mL of MACS™ buffer.

After separation, A2B5+ or NCAM+ cells are maintained on plates coated with poly-lysine and laminin in DMEM/F12 (Biowhittaker) supplemented with N2 (Gibco 17502–014), B27 (Gibco 17504–010) and the factors indicated. Source of the factors is shown in Table 2.

TABLE 2

Factors used for Neural Cell Culture

| Growth Factor | Source | Working Concentration |
|---|---|---|
| human EGF | R&D Systems | 10 ng/mL |
| human bFGF | Gibco | 10–25 ng/mL |
| human CNTF | R&D Systems | 1–10 ng/mL |
| human PDGF | R&D Systems | 1 ng/mL |
| human IGF-I | R&D Systems | 1 ng/mL |

RT-PCR analysis of expression at the transcription level is conducted as follows: RNA is extracted from the cells using RNAeasy Kit™ (Qiagen) as per manufacturer's instructions. The final product is then digested with DNAse to get rid of contaminating genomic DNA. The RNA is incubated in RNA guard (Pharmacia Upjohn) and DNAse I (Pharmacia Upjohn) in buffer containing 10 mM Tris ph 7.5, 10 mM $MgCl_2$, and 5 mM DDT at 37° C. for 30–45 min. To remove protein from the sample, phenol chloroform extraction is performed, and the RNA precipitated with 3 M sodium acetate and 100% cold ethanol. The RNA is washed with 70% ethanol, and the pellet is air-dried and resuspended in DEPC-treated water.

For the reverse transcriptase (RT) reaction, 500 ng of total RNA is combined with a final concentration of 1× First Strand Buffer (Gibco), 20 mM DDT and 25 µg/mL random hexamers (Pharmacia Upjohn). The RNA is denatured for 10 min at 70° C., followed by annealing at room temperature for 10 min. dNTPs are added at a final concentration of 1 mM along with 0.5 µL of Superscript II RT (Gibco), incubated at 42° C. for 50 minute, and then heat-inactivated at 80° C. for 10 min. Samples are then stored at −20° C. till they are processed for PCR analysis. Standard polymerase chain reaction (PCR) is performed using primers specific for the markers of interest in the following reaction mixture: cDNA 1.0 µL, 10× PCR buffer (Gibco) 2.5 µL, 10×$MgCl_2$ 2.5 µL, 2.5 mM dNTP 3.0 µL, 5 µM 3'-primer 1.0 µL, 5 µM 5'-primer, 1.0 µL, Taq 0.4 µL, DEPC-water 13.6 µL.

Example 1
NCAM-positive Cells

This experiment focused on determining whether the human embryonic stem cells (hES) could undergo directed differentiation to NCAM-positive progenitor cells. The hES cells were harvested either from mEF-supported cultures or feeder-free cultures, and then differentiated via embryoid body (EB) formation in suspension culture using medium containing 20% FBS. The EBs were then plated intact onto fibronectin in DMEM/F12 medium, supplemented with N2 supplement (Gibco) and 25 ng/mL human bFGF. After culturing for about 2–3 days, NCAM-positive cells and A2B5-positive cells were identified by immunostaining.

Magnetic bead sorting and immunopanning were both successful in enriching NCAM-positive cells. The starting population of cells typically contained 25–72% NCAM-positive cells. After immuno-isolation, the NCAM-positive proportion was enriched to 43–72%. Results are shown in Table 3.

TABLE 3

Differentiation and Sorting Conditions for NCAM positive Cells

| hES Cell Line used for Differentiation | Factors used in Differentiation Culture | Type of Sort | Before sort | Cells staining positively for NCAM Positive sort | Negative sort |
|---|---|---|---|---|---|
| H13 p28 | CFN | bead sort | 33 | 92 | 41 |
| H13 p28 | CFN | panning | 25 | n/a | n/a |
| H9 p32 | CFN | panning | 64 | 72 | 51 |
| H1 p32 | CFN | bead sort | 27 | 77 | 9 |
| H9 p19 | CFN | bead sort | 58 | 76 | 32 |
| H9 p31 545.184 | CFN | bead sort | 50 | 91 | 67 |
| H1 p40 545.185 | CFN | bead sort A | 65 | 89 | 31 |
| H1 p40 545.185 | CFN | bead sort B | 63 | 81 | 33 |
| H7NG p28/4 545.187 | CFN | bead sort A | 53 | 92 | 45 |
| H7NG p28/4 545.187 | CFN | bead sort A | 72 | 87 | 50 |
| H1 p39 545.189 | CFNIP | bead sort | 16 | 43 | 6 |
| H7 p32 667.004 | CFNIP | bead sort | 25 | 73 | 10 |
| H1 p43 667.010 | CFNIP | bead sort | 47 | 86 | 31 |
| H1 p44 667.012 | CFNIP | bead sort | 52 | 89 | 34 |
| H1 p46 667.020 | EPFI | bead sort | 60 | 23 | 8 |
| H1 p47 667.031 | EPFI-EPFI | bead sort | 53 | 91 | 27 |
| H1 p47 667.033 | CFN-F | bead sort | 41 | 76 | 24 |
| H9 p40 MG 667.038 | EPFI | bead sort | 55 | 80 | 25 |

Factor abbreviations:
I — insulin-like growth factor (IGF-1)
P — platelet-derived growth factor (PDGF)
C — ciliary neurotrophic factor (CNTF)
T — thyroid hormone $T_3$
F — basic fibroblast growth factor (bFGF)
Ra — retinoic acid
N — neurotrophin 3 (NT3)
Fk — Forskolin In the first 10 experiments shown, NCAM positive cells retrieved from the sort were plated on poly-L-lysine/laminin in DMEM/F12 with N2 and B27 supplements and 2 mg/mL BSA, 10 ng/mL human CNTF, 10 ng/mL human bFGF and 1 ng/mL human NT-3. In subsequent experiments, cells were maintained in DMEM/F12 with N2 and B27 supplements and 10 ng/mL EGF, 10 ng/mL bFGF, 1 ng/mL PDGF, and 1 ng/mL IGF-1.

FIG. 1 (Upper Panel) shows the growth curves for the NCAM positive cells. The cells studied in this experiment were prepared by forming embryoid bodies in 20% FBS for 4 days in suspension, then plating onto a fibronectin matrix in DMEM/F12 with N2 and B27 supplements and 25 ng/mL bFGF for 2–3 days. The cells were then positively sorted for NCAM expression, and maintained in a medium containing CNTF, bFGF, and NT3. The sorted cells did not show increased survival relative to the unsorted population. It was found that some of the NCAM positive cells also express β-tubulin III, indicating that these cells have the capacity to form neurons. They also had morphology characteristic of neuronal cells. There were also A2B5 positive cells within this population, which may represent glial progenitor cells. However, very few cells were positive for GFAP, a marker for astrocytes. Although this cell population proliferated in culture, the proportion of NCAM positive cells (and the capacity to form neurons) diminished after several passages.

Example 2

A2B5-positive Cells

Cells in this experiment were immunoselected for the surface marker A2B5. hES cells were induced to form EBs in 20% FBS. After 4 days in suspension, the EBs were plated onto fibronectin in DMEM/F12 with N2 and B27 supplemented with 10 ng/mL human EGF, 10 ng/mL human bFGF, 1 ng/mL human IGF-1, and 1 ng/mL human PDGF-AA. After 2–3 days in these conditions, 25–66% of the cells express A2B5. This population is enriched by magnetic bead sorting to 48–93% purity (Table 4).

TABLE 4

Differentiation and Sorting Conditions for A2B5-positive Cells

| hES Cell Line used for Differentiation | Factors used in Differentiation Culture | Type of Sort | Cells staining positively for NCAM | | |
|---|---|---|---|---|---|
| | | | Before sort | Positive sort | Negative sort |
| H7 p32 667.004 | CFNIP | bead sort | 25 | 77 | 10 |
| H1 p43 667.010 | CENIP | bead sort | 62 | n/a | 50 |
| H1 p44 667.012 | CFNIP | bead sort | 56 | 89 | 32 |
| H1 p46 667.020 | EPFI | bead sort | 27 | 48 | 2 |
| H1 p47 667.032 | EPFI | bead sort | 57 | 93 | 30 |
| H9 p40 MG 667.038 | EPFI | bead sort | 66 | 93 | 41 |
| H9 p42 667.041 | EPFI | bead sort | 27 | 70 | 6 |

Factor abbreviations:
I — insulin-like growth factor (IGF-1)
P — platelet-derived growth factor (PDGF)
C — ciliary neurotrophic factor (CNTF)
T — thyroid hormone $T_3$
F — basic fibroblast growth factor (bFGF)
Ra — retinoic acid
N — neurotrophin 3 (NT3)
Fk — Forskolin FIG. 2 shows an exemplary procedure for obtaining A2B5-positive cells. Abbreviations used: MEF-CM=medium conditioned by culturing with mouse embryonic fibroblasts; +/−SHH=with or without sonic hedgehog; D/F12=DMEM/F12 medium; N2 and B27, culture supplements (Gibco); EPFI=growth factors EGF, PDGF, bFGF, and IGF-1; PLL=poly-L lysine substrate; PLL/FN=substrate of poly-L lysine and fibronectin.

FIG. 1 (Lower Panel) shows the growth curves for the sorted A2B5-positive cells. The cells were maintained in the same media formulation on poly-l-lysine coated plates. The cells proliferate when serially passaged.

Example 3

Maturation of A2B5-positive Cells

A2B5-positive cells were induced to differentiate by the addition of forskolin. These cells have been assessed through different culture passages, as shown in Table 5.

TABLE 5

Phenotypic Features of Mature Neural Cells

| No. of passages after A2B5 sort | Method of Maturation | Neuron-like morphology visible | β-tubulin | GFAP | GalC | A2B5 | NCAM |
|---|---|---|---|---|---|---|---|
| 1 | PICNT + Fk 4 days | yes | 38 ± 9% | | 13 ± 7% | 79 ± 3% | 28 ± 6% |
| 3 | PICNT + Fk 2 days | yes | +++ | | + | +++++ | ++ |
| 7 | +/− EF +/− serum | yes | + | + | ++ | +++ | — |

Factor abbreviations:
I — insulin-like growth factor (IGF-1)
P — platelet-derived growth factor (PDGF)
C — ciliary neurotrophic factor (CNTF)
T — thyroid hormone $T_3$
F — basic fibroblast growth factor (bFGF)
Ra — retinoic acid
N — neurotrophin 3 (NT3)
Fk — Forskolin Even though the cells were sorted for A2B5 expression, the population demonstrated the capacity to generate not only oligodendrocytes, and astrocytes, but also a large proportion of neurons. This is surprising: it was previously thought that A2B5 expressing cells were glial precursors, and would give rise to oligodendrocytes, and astrocytes—while NCAM expressing cells were neuronal precursors, giving rise to mature neurons. This experiment demonstrates that pPS cells can be differentiated into a cell population that proliferates repeatedly in culture, and is capable of generating neurons and glia.

Example 4
Transplantation of Differentiated Cells into the Mammalian Brain

Transplantation of neural precursor cells was done using cells derived from two hES cell lines: the line designated H1, and a genetically altered line designated H7NHG. The H7NHG cell line carries an expression cassette that permits the cells to constitutively express green fluorescent protein (GFP).

Neonatal Sprague Dawley rats received unilateral intrastriatal implants of one of the following cell populations:
 undifferentiated hES cells
 embryoid bodies derived from hES cells
 neural precursors sorted for NCAM expression (Example 1)
 neural precursors sorted for A2B5 expression (Example 2)

Control animals received grafts of irradiated mouse embryonic fibroblasts upon which the undifferentiated hES cells were maintained. To determine if cell proliferation occurred after grafting, some animals were pulsed with intraperitoneal injections of BrdU, commencing 48 h prior to sacrifice. Fourteen days after transplantation, the rats were transcardially perfused with 4% paraformaldehyde and the tissue was processed for immunohistochemical analysis.

FIG. 3 shows the fluorescence observed in sections from animals administered cells expressing GFP. Surviving cells were detected in all transplanted groups. The undifferentiated cells presented as large cell masses, suggesting unregulated growth with areas of necrosis and vacuolation of surrounding tissue (Left-side Panels). Immunostaining for AFP in an animal transplanted with HI cells showed that undifferentiated hES cells transformed into visceral endoderm after transplantation. Embryoid bodies remained in the graft core with little migration, and were also surrounded by areas of necrosis. (Middle Panels). In contrast, sorted NCAM-positive cells appeared as single cells and showed some degree of migration distal to the site of implantation.

Example 5
Differentiation to Mature Neurons

To generate terminally differentiated neurons, the first stage of differentiation was induced by forming embryoid bodies in FBS medium with or without 10 μM retinoic acid (RA). After 4 days in suspension, embryoid bodies were plated onto fibronectin-coated plates in defined medium supplemented with 10 ng/mL human EGF, 10 ng/mL human bFGF, 1 ng/mL human PDGF-AA, and 1 ng/mL human IGF-1. The embryoid bodies adhered to the plates, and cells began to migrate onto the plastic, forming a monolayer.

After 3 days, many cells with neuronal morphology were observed. The neural precursors were identified as cells positive for BrdU incorporation, nestin staining, and the absence of lineage specific differentiation markers. Putative neuronal and glial progenitor cells were identified as positive for polysialylated NCAM and A2B5. Forty one to sixty percent of the cells expressed NCAM, and 20–66% expressed A2B5, as measured by flow cytometry. A subpopulation of the NCAM-positive cells was found to express β-tubulin III and MAP-2. There was no co-localization with glial markers such as GFAP or GalC. The A2B5 positive cells appeared to generate both neurons and glia. A subpopulation of the A2B5 cells expressed β-tubulin III or MAP-2, and a separate subpopulation expressed GFAP. Some of the cells with neuronal morphology double-stained for both A2B5 and NCAM. Both the NCAM positive and A2B5 positive populations contained far more neurons than glia.

The cell populations were further differentiated by replating the cells in a medium containing none of the mitogens, but containing 10 ng/mL Neurotrophin-3 (NT-3) and 10 ng/mL brain-derived neurotrophic factor (BDNF). Neurons with extensive processes were seen after about 7 days. Cultures derived from embryoid bodies maintained in retinoic acid (RA) showed more MAP-2 positive cells (~26%)

than those maintained without RA (~5%). GFAP positive cells were seen in patches. GalC positive cells were identified, but the cells were large and flat rather than having complex processes.

A summary of cell types and markers expressed at different stages of differentiation is provided in Table 6.

TABLE 6

| Phenotypic Markers (Immunocytochemistry) | | |
|---|---|---|
| Undifferentiated hES colonies | NCAM-positive progenitors | A2B5 positive progenitors |
| Tra-1-60 + | Nestin subset | Nestin subset |
| Tra-1-81 + | A2B5 subset | NCAM subset |
| SSEA-4 + | β-tubulin III subset | β-tubulin III subset |
| β-tubulin III + | Map-2 subset | Map-2 subset |
| Nestin — | GFAP — | GFAP rare |
| Map-2 — | GalC — | GalC — |
| Neurofilament (NF) — | AFP — | AFP — |
| GFAP — | muscle-specific actin — | muscle-specific actin — |
| GalC — | | |
| α-fetoprotein — | | |
| muscle-specific actin | | |
| NCAM — | | |
| A2B5 — | | |
| Neurons | Astrocytes | Oligodendrocytes |
| β-tubulin III + | GFAP + | GalC + |
| MAP-2 + | | |
| Neurofilament (NF) subset | | |
| GABA subset | | |
| tyrosine hydroxylase subset | | |
| glutamate subset | | |
| glycine subset | | |

The presence of neurotransmitters was also assessed. GABA-immunoreactive cells were identified that co-expressed β-tubulin III or MAP2, and had morphology characteristic of neuronal cells. Occasional GABA-positive cells were identified that did not co-express neuronal markers, but had an astrocyte-like morphology. Neuronal cells were identified that expressed both tyrosine hydroxylase (TH) and MAP-2. Synapse formation was identified by staining with synaptophysin antibody.

FIG. 4 shows TH staining in cultures differentiated from the H9 line of human ES cells. Embryoid bodies were maintained in 10 μM retinoic acid for 4 days, then plated onto fibronectin coated plates in EGF, basic FGF, PDGF and IGF for 3 days. They were next passaged onto laminin in N2 medium supplemented with 10 ng/mL NT-3 and 10 ng/mL BDNF, and allowed to differentiate further for 14 days. The differentiated cells were fixed with 2% formaldehyde for 20 min at room temp, and then developed using antibody to TH, a marker for dopaminergic cells.

Example 6

Calcium Imaging

Standard fura-2 imaging of calcium flux was used to investigate the functional properties of the hES cell derived neurons. Neurotransmitters studied included GABA, glutamate (E), glycine (G), elevated potassium (50 mM K$^+$ instead of 5 mM K$^+$), ascorbic acid (control), dopamine, acetylcholine (ACh) and norepinephrine. The solutions contained 0.5 mM of the neurotransmitter (except ATP at 10 μM) in rat Ringers (RR) solution: 140 mM NaCl, 3 mM KCl, 1 mM MgCl$_2$, 2 mM CaCl$_2$, 10 mM HEPES buffer, and 10 mM glucose. External solutions were set to pH 7.4 using NaOH. Cells were perfused in the recording chamber at 1.2–1.8 mL/min, and solutions were applied by bath application using a 0.2 mL loop injector located ~0.2 mL upstream of the bath import. Transient rises in calcium were considered to be a response if the calcium levels rose above 10% of the baseline value within 60 sec of application, and returned to baseline within 1–2 min.

FIG. 5 shows the response of neural-restricted precursors to various neurotransmitters. Panel A shows the ratio of emission data from single cells on two different coverslips. Addition of the neurotransmitters is indicated above by labeled triangles.

Panel B shows the frequency of cells tested that responded to specific neurotransmitters. Panel C shows the combinations of neurotransmitter responses observed. Of the 53 cells tested, 26 responded to GABA, acetylcholine, ATP and elevated potassium. Smaller subsets of the population responded to other combinations of agonists. Only 2 of the cells failed to respond to any of the agonists applied.

Example 7

Electrophysiology

Standard whole-cell patch-clamp technique was conducted on the hES cell derived neurons, to record ionic currents generated in voltage-clamp mode and the action potential generated in current-clamp mode. The external bath solution was rat Ringers solution (Example 6). The internal solution was 75 mM potassium-aspartate, 50 mM KF, 15 mM NaCl, 11 mM EGTA, and 10 mM HEPES buffer, set to pH 7.2 using KOH.

All 6 cells tested expressed sodium and potassium currents, and fired action potentials. Passive membrane properties were determined with voltage steps from −70 to −80 mV; and produced the following data: average capacitance $(C_m)$=8.97±1.17 pF; membrane resistance $(R_m)$= 487.8±42.0 MΩ; access resistance $(R_a)$=23.4±3.62 MΩ. Ionic currents were determined by holding the cells at −100 mV, and stepping to test voltages between −80 and 80 mV in 10 mV increments, producing the following data: average sodium current $I_{Na}$=−531.8±136.4 pA; average potassium current $I_K$=441.7±113.1 pA; $I_{Na}$(density)=−57.7±7.78 pA/pF; $I_K$(density)=48.2±10.4 pA/pF.

FIG. 6 shows results from a typical experiment. Panel A shows sodium and potassium currents observed in two cells depolarized to test potentials between −80 and 80 mV from a holding potential of −100 mV. Panel B shows the inward (Na⁺) and outward (K⁺) peak current-voltage relationships observed. Sodium current activates between −30 and 0 mV, reaching a peak at −10 or 0 mV. Potassium current activates above −10 mV, becoming equal or larger in magnitude than the sodium current at voltages between 20 and 40 mV. Panel C shows action potentials generated by the same cells n response to depolarizing stimuli. Cell membranes were held at voltages between −60 and −100 mV in −80 or −150 pA of current, and depolarized for short durations Example 8
Dopaminergic Cells Derived from Neural Progenitor Cells Embryoid bodies were cultured in suspension with 10 μM retinoic acid for 4 days, then plated into defined medium supplemented with EGF, bFGF, PDGF, and IGF-1 for 3–4 days. Cells were then separated by magnetic bead sorting or immunopanning into A2B5-positive or NCAM-positive enriched populations.

The immuno-selected cells were maintained in defined medium supplemented with 10 ng/mL NT-3 and 10 ng/mL BDNF. After 14 days, 25±4% of the NCAM-sorted cells were MAP-2 positive—of which 1.9±0.8% were GABA-positive, and 3±1% were positive for tyrosine hydroxylase (TH): the rate-limiting enzyme for dopamine synthesis, generally considered to be representative of dopamine-synthesizing cells.

In the cell population sorted for NCAM, the cells that were NCAM+ve did not express glial markers, such as GFAP or GalC. These data indicate that a population comprising neuron restricted precursors can be isolated directly from hES cell cultures, essentially uncontaminated with glial precursors.

Cells sorted for A2B5, on the other hand, have the capacity to generate both neurons and astrocytes. After the enrichment, the cells were placed into defined media supplemented with NT-3 and BDNF and allowed to differentiate for 14 days. Within the first 1–2 days after plating, cells in the A2B5 enriched population began to extend processes. After two weeks, cells took on the morphology of mature neurons, and 32±3% of the cells were MAP-2 positive. Importantly, 3±1% of the MAP-2 cells were TH-positive, while only 0.6±0.3% were GABA immunoreactive. These data indicate that a population of cells can be obtained from hES cells that comprise progenitors for both astrocytes and neurons, including those that synthesize dopamine.

Further elaboration of conditions for obtaining TH-expression neurons was conduced as follows. Embryoid bodies were generated from confluent hES cells of the H7 line at passage 32 by incubating in 1 mg/mL collagenase (37° C., 5–20 min), scraping the dish, and placing the cells into non-adherent culture plates (Costar®). The resulting EBs were cultured in suspension in media containing FBS and 10 μM all-trans retinoic acid. After four days, the aggregates were collected and allowed to settle in a centrifuge tube. The supernatant was then aspirated, and the aggregates were plated onto poly L-lysine and fibronectin coated plates in proliferation medium (DMEM/F12 1:1 supplemented with N2, half-strength B27, 10 ng/mL EGF (R & D Systems), 10 ng/mL bFGF (Gibco), 1 ng/mL PDGF-AAA (R & D Systems), and 1 ng/mL IGF-1 (R & D Systems).

The EBs were allowed to attach and proliferate for three days; then collected by trypsinizing ~1 min (Sigma) and plated at 1.5×10⁵ cells/well onto poly I-lysine and laminin coated 4-well chamber slides in proliferation medium for one day. The medium was then changed to Neural Basal medium supplemented with B27, and one of the following growth cocktails:

10 ng/mL bFGF (Gibco), 10 ng/mL BDNF, and 10 ng/mL NT-3

10 ng/mL bFGF, 5000 ng/mL sonic hedgehog, and 100 ng/mL FGF8b 10 ng/mL bFGF alone The cells were maintained in these conditions for 6 days, with feeding every other day. On day 7, the medium was changed to Neural Basal medium with B27, supplemented with one of the following cocktails:

10 ng/mL BDNF, 10 ng/mL NT-3

1 μM cAMP, 200 μM ascorbic acid

1 μM cAMP, 200 μM ascorbic acid, 10 ng/mL BDNF, 10 ng/mL NT-3

The cultures were fed every other day until day 12 when they were fixed and labeled with anti-TH or MAP-2 for immunocytochemistry. Expression of the markers was quantified by counting four fields in each of three wells using a 40× objective lens.

Results are shown in Table 7. Initial culturing in bFGF, BDNF and NT-3 yielded the highest proportion of TH positive cells.

TABLE 7

Conditions for Producing Dopaminergic Neurons

| Culture conditions | | % MAP-2 positive | % MAP-2 cells that are TH positive |
|---|---|---|---|
| days 1–6 | days 6–12 | | |
| B, N, F | B, N | 26% | 5.5% |
| B, N, F | CA, AA | 35% | 4.0% |
| B, N, F | CA, AA, B, N | 25% | 8.7% |
| F, F8, S | B, N | 37% | 3.7% |
| F, F8, S | CA, AA | 34% | 3.9% |
| F, F8, S | CA, AA, B, N | 21% | 5.8% |
| F | B, N | 28% | 3.5% |
| F | CA, AA | 26% | 4.1% |
| F | CA, AA, B, N | 22% | 5.7% |

Factor abbreviations:
B - brain-derived neurotrophic factor (BDNF)
S - sonic hedgehog
F - basic fibroblast growth factor (bFGF)
F - FGF8
N - neurotrophin 3 (NT3)
CA - cAMP
AA - ascorbic acid It is understood that certain adaptations of the invention described in this disclosure are a matter of routine optimization for those skilled in the art, and can be implemented without departing from the spirit of the invention, or the scope of the appended claims.

What is claimed as the invention is:

1. A method for producing a neural cell population from human embryonic stem (hES) cells, comprising culturing hES cells in a medium containing one or more added neurotrophins and one or more added nitrogens, thereby producing a population in which at least 60% of the cells express A2B5, polyslalylated NCAM, MAP-2, or Nestin.

2. The method of claim 1, wherein the added neurotrophins include neurotrophin 3 (NT-3) or brain-derived neurotrophic factor (BDNF).

3. The method of claim 2, wherein the added neurotrophins include both NT-3 and BDNF.

4. The method at claim 1, wherein the added mitogens include a mitogen selected from epidermal growth factor (EGF), basic fibroblast growth factor (bFGF), platelet-derived growth factor (PDGF), and insulin-like growth factor 1 (IGF-1).

5. The method of claim 4, wherein the added mitogens include both PDGF and IGF-1.

6. The method of claim 1, wherein the hES cells are cultured on fibronectin.

7. The method of claim 1, comprising selecting and propagating cells that are positive for polyslalylated NCAM.

8. The method of claim 1, wherein the produced cell population is at least 60% positive for polystalylated NCAM.

9. The method of claim 1, wherein the produced cell population is at least 90% positive for polystalylated NCAM.

10. The method of claim 1, wherein the produced cell population is at least 38% β-tubulin III positive.

11. The method of claim 1, wherein the produced cell population has the characteristic that culturing it in the presence of neurotrophins maintains capacity of the cells to proliferate and to form tyrosine hydroxylase positive neurons upon differentiation.

12. The method of claim 1, wherein the produced cell population is essentially free of undifferentiated hES cells.

13. The method of claim 1, further comprising differentiating the cells into a population that contains at least 30% neurons.

14. The method of claim 1, further comprising differentiating the cells into a population that contains at least 30% MAP-2 positive cells.

15. The method of claim 14, wherein at least 3% of the differentiated cells positive for MAP-2 are also positive for tyrosine hydroxylase.

16. The method of claim 14, wherein at least 8% of the differentiated cells positive for MAP-2 are also positive for tyrosine hydroxylase.

17. The method of claim 14, wherein the differentiating comprises culturing the cells in a medium containing one or more factors selected from neurotrophins, cAMP, and ascorbic acid for at least 3 days, in the absence of added mitogens.

18. The method of claim 1, wherein the differentiated cell population comprises sensory or motor neurons.

19. The method of claim 1, wherein the differentiated cell population comprises oligodendrocytes or astrocytes.

20. The method of claim 1, further comprising combining the produced cell population with a pharmaceutically compatible excipient.

21. A method for producing a neural cell population from human embryonic stem (hES) cells, comprising initiating differentiation of the hES cells into a heterogeneous population of precursor cells, then culturing the initiated cells in a medium containing one or more added neurotrophins and one or more added mitogens, thereby producing a population in which at least 60% of the cells express A2B5, polysialylated NCAM, MAP-2, or Nestin.

22. The method of claim 21, wherein the added neurotrophins include neurotrophin 3 (NT-3) or brain-derived neurotrophic factor (BDNF).

23. The method of claim 22, wherein the added neurotrophins include both NT-3 and BDNF.

24. The method of claim 21, wherein the added mitogens include a mitogen selected from epidermal growth factor, (EGF), basic fibroblast growth factor (bFGF), platelet-derived growth factor (PDGF), and insulin-like growth factor 1 (IGF-1).

25. The method of claim 24, wherein the added mitogens include both PDGF and IGF-1.

26. The method of claim 21, wherein the precursor cells are cultured on fibronectin.

27. The method of claim 21, wherein differentiation is initiated by culturing the hES cells in a medium containing retinoic acid before culturing with the neurotrophins and mitogens.

28. The method of claim 21, wherein differentiation is initiated by culturing the cells as embryold bodies before culturing with the neurotrophins and mitogens.

29. The method of claim 21, wherein differentiation is initiated by culturing the cells as cell aggregates before culturing with the neurotrophins and mitogens.

30. The method of claim 21, comprising selecting and propagating cells that are positive for polysialylated NCAM.

31. The method of claim 21, wherein the produced cell population is at least 60% positive for polysialytated NCAM.

32. The method of claim 21, wherein the produced cell population is at least 90% positive for polysialylated NCAM.

33. The method of claim 21, wherein the produced cell population is at least 38% β-tubulin III positive.

34. The method of claim 21, wherein the produced cell population has the characteristic that culturing it in the presence of neurotrophins maintains capacity of the cells to proliferate and to form tyrosine hydroxylase positive neurons upon differentiation.

35. The method of claim 21, wherein the produced cell population is essentially free of undifferentiated hES cells.

36. The method of claim 21, further comprising differentiating the cells into a population that contains at least 30% neurons.

37. The method of claim 21, further comprising differentiating the cells into a population that contains at least 30% MAP-2 positive cells.

38. The method of claim 37, wherein at least 3% of the differentiated cells positive for MAP-2 are also positive for tyrosine hydroxylase.

39. The method of claim 37, wherein at least 8% of the differentiated cells positive for MAP-2 are also positive for tyrosine hydroxylase.

40. The method of claim 37, wherein the differentiating comprises culturing the cell in a medium containing one or more factors selected from neurotrophins, cAMP, and ascorbic acid for at least 3 days, in the absence of added mitogens.

41. The method of claim 21, wherein the differentiated cell population comprises sensory or motor neurons.

42. The method of claim 21, wherein the differentiated cell population comprises oligodendrocytes or astrocytes.

43. The method of claim 21, further comprising combining the produced cell population with a pharmaceutically compatible excipient.

* * * * *

UNITED STATES PATENT AND TRADEMARK OFFICE
CERTIFICATE OF CORRECTION

PATENT NO. : 6,833,269 B2 Page 1 of 1
APPLICATION NO. : 09/872183
DATED : December 21, 2004
INVENTOR(S) : Melissa K. Carpenter It is certified that error appears in the above-identified patent and that said Letters Patent is hereby corrected as shown below:

Column 32, line 58, the word "nitrogens" should read --mitogens--;
    line 60, the word "polyslalylated" should read --polysialylated--; and
    line 66, the word "at" should read --of--.

Column 33, line 9, the word "polyslalylated" should read --polysialylated--;
    line 11, the word "polystalylated" should read --polysialylated--;
    line 14, the word "polystalylated" should read --polysialylated--; and
    line 49, the word "initialing" should read --initiating--.

Column 34, line 15, the word "embryold" should read --embryoid--;
    line 23, the word "polysialytated" should read --polysialylated--; and
    line 49, the word "cell" should read --cells--.

Signed and Sealed this

Seventeenth Day of April, 2007

JON W. DUDAS
*Director of the United States Patent and Trademark Office*